US012268467B2

(12) United States Patent
Yoo et al.

(10) Patent No.: US 12,268,467 B2
(45) Date of Patent: *Apr. 8, 2025

(54) DELIVERY SYSTEM

(71) Applicant: Wake Forest University Health Sciences, Winston-Salem, NC (US)

(72) Inventors: James J. Yoo, Winston-Salem, NC (US); Anthony Atala, Winston-Salem, NC (US); Kyle W. Binder, Winston-Salem, NC (US); Weixin Zhao, Winston-Salem, NC (US); Dennis Dice, Yadkinville, NC (US); Tao Xu, El Paso, TX (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1535 days.

This patent is subject to a terminal disclaimer.

(21) Appl. No.: 16/694,017

(22) Filed: Nov. 25, 2019

(65) Prior Publication Data

US 2020/0101273 A1 Apr. 2, 2020

Related U.S. Application Data

(63) Continuation of application No. 12/986,812, filed on Jan. 7, 2011, now Pat. No. 10,500,384.

(Continued)

(51) Int. Cl.
*A61B 5/00* (2006.01)
*A61M 35/00* (2006.01)
(Continued)

(52) U.S. Cl.
CPC ........... *A61B 5/0064* (2013.01); *A61M 35/00* (2013.01); *B41J 3/4073* (2013.01); *A61B 5/445* (2013.01);
(Continued)

(58) Field of Classification Search
None
See application file for complete search history.

(56) References Cited

U.S. PATENT DOCUMENTS 3,830,228 A 8/1974 Foner
4,727,494 A 2/1988 Buote
(Continued)

FOREIGN PATENT DOCUMENTS

EP 1459782 9/2004
WO 2004084828 A2 10/2004
(Continued)

OTHER PUBLICATIONS

Grant, I. et al. "The co-application of sprayed cultured autologous keratinocytes and autologous fibrin sealant in a porcine wound model", British Journal of Plastic Surgery, 2002, vol. 55, pp. 219-227.

(Continued)

*Primary Examiner* — Bradley H Philips
(74) *Attorney, Agent, or Firm* — Myers Bigel, P.A.

(57) ABSTRACT

Provided herein is a delivery system, including: (a) an optical sensor configured to detect data useful to create a map of a bodily surface; and (b) a printer operatively associated with the optical sensor and configured to deliver compositions (optionally including cells) to the bodily surface based upon the data or map. Methods of forming a tissue on a bodily surface of a patient in need thereof are also provided, as are methods, systems and computer program products useful for processing bodily surface data.

20 Claims, 6 Drawing Sheets

Related U.S. Application Data

(60) Provisional application No. 61/293,481, filed on Jan. 8, 2010.

(51) Int. Cl.
*B41J 3/407* (2006.01)
*A61B 17/00* (2006.01)
*A61B 17/322* (2006.01)
*A61B 34/10* (2016.01)

(52) U.S. Cl.
CPC ............... *A61B 2017/00747* (2013.01); *A61B 2017/00969* (2013.01); *A61B 2017/3225* (2013.01); *A61B 2034/105* (2016.02); *A61B 2034/108* (2016.02); *A61M 35/20* (2019.05)

(56) References Cited

U.S. PATENT DOCUMENTS

| | | | |
|---|---|---|---|
| 4,738,425 | A | 4/1988 | Foster |
| 5,355,439 | A | 10/1994 | Bernstein et al. |
| 5,536,084 | A | 7/1996 | Curtis et al. |
| 5,685,821 | A | 11/1997 | Pike |
| 5,696,887 | A | 12/1997 | Bernstein et al. |
| 5,702,444 | A | 12/1997 | Struthers et al. |
| 5,709,854 | A | 1/1998 | Griffith-Cima et al. |
| 5,716,404 | A | 2/1998 | Vacanti |
| 5,776,050 | A | 7/1998 | Chen et al. |
| 5,971,976 | A | 10/1999 | Wang et al. |
| 6,055,704 | A | 5/2000 | Leibman |
| 6,165,487 | A | 12/2000 | Ashkar et al. |
| 6,201,065 | B1 | 3/2001 | Pathak et al. |
| 6,205,243 | B1 | 3/2001 | Migdal et al. |
| 6,381,026 | B1 | 4/2002 | Schiff et al. |
| 6,428,802 | B1 | 8/2002 | Atala |
| 6,438,272 | B1 | 8/2002 | Huang et al. |
| 6,482,435 | B1 | 11/2002 | Stratton et al. |
| 6,537,567 | B1 | 3/2003 | Niklason et al. |
| 6,562,326 | B1 | 5/2003 | Miller |
| 6,589,728 | B2 | 7/2003 | Csete et al. |
| 6,676,654 | B1 | 1/2004 | Balle-Petersen et al. |
| 6,783,964 | B2 | 8/2004 | Opara |
| 6,788,210 | B1 | 9/2004 | Huang et al. |
| 6,856,407 | B2 | 2/2005 | Knighton et al. |
| 6,923,833 | B2 | 8/2005 | Wasielewski |
| 6,969,480 | B2 | 11/2005 | Dalton et al. |
| 6,986,739 | B2 * | 1/2006 | Warren ............... C12M 21/08 118/683 |
| 6,991,652 | B2 | 1/2006 | Burg |
| 6,995,013 | B2 | 2/2006 | Connelly et al. |
| 7,019,192 | B2 | 3/2006 | Gertzman et al. |
| 7,051,654 | B2 | 5/2006 | Boland et al. |
| 7,150,989 | B2 | 12/2006 | Goldman et al. |
| 7,625,198 | B2 | 12/2009 | Lipson et al. |
| 7,630,089 | B2 | 12/2009 | Babayoff et al. |
| 7,643,025 | B2 | 1/2010 | Lange |
| 7,705,291 | B2 | 4/2010 | Al-Moosawi et al. |
| 8,021,876 | B2 | 9/2011 | Atala et al. |
| 9,056,093 | B2 | 6/2015 | Atala et al. |
| 10,537,689 | B2 | 1/2020 | Yoo et al. |
| 11,759,579 | B2 | 9/2023 | Yoo et al. |
| 2003/0100824 | A1 | 5/2003 | Warren et al. |
| 2003/0170285 | A1 | 9/2003 | Veazey et al. |
| 2003/0175410 | A1* | 9/2003 | Campbell ............... A61L 27/38 623/23.72 |
| 2004/0053869 | A1 | 3/2004 | Andrews et al. |
| 2004/0115810 | A1 | 6/2004 | Luu et al. |
| 2004/0161412 | A1 | 8/2004 | Penn et al. |
| 2004/0214319 | A1 | 10/2004 | Pebay et al. |
| 2004/0237822 | A1 | 12/2004 | Boland et al. |
| 2004/0241856 | A1 | 12/2004 | Cooke |
| 2004/0253365 | A1 | 12/2004 | Warren et al. |
| 2005/0054893 | A1 | 3/2005 | Atala et al. |
| 2005/0124003 | A1 | 6/2005 | Atala et al. |
| 2005/0131212 | A1 | 6/2005 | Sieg et al. |
| 2005/0153941 | A1 | 7/2005 | Miyabayashi et al. |
| 2005/0202428 | A1 | 9/2005 | Andrews et al. |
| 2005/0227353 | A1 | 10/2005 | Mummery |
| 2005/0237581 | A1 | 10/2005 | Knighton et al. |
| 2005/0266553 | A1 | 12/2005 | Pebay et al. |
| 2006/0006018 | A1 | 1/2006 | Fleming et al. |
| 2006/0013804 | A1 | 1/2006 | Megeney et al. |
| 2006/0156978 | A1 | 7/2006 | Lipson et al. |
| 2007/0031384 | A1 | 2/2007 | Atala et al. |
| 2007/0169307 | A1 | 7/2007 | Yu et al. |
| 2008/0033410 | A1 | 2/2008 | Rastegar et al. |
| 2008/0070304 | A1 | 3/2008 | Forgacs et al. |
| 2009/0117087 | A1 | 5/2009 | Carroll et al. |
| 2009/0118600 | A1 | 5/2009 | Ortiz et al. |
| 2009/0208466 | A1 | 8/2009 | Yoo et al. |
| 2009/0208577 | A1 | 8/2009 | Xu et al. |
| 2010/0160183 | A1 | 6/2010 | Xu et al. |
| 2011/0212501 | A1 | 9/2011 | Yoo |
| 2011/0280914 | A1 | 11/2011 | Prestwich et al. |
| 2013/0017564 | A1 | 1/2013 | Guillemot et al. |
| 2014/0012225 | A1 | 1/2014 | Yoo et al. |
| 2015/0224226 | A1 | 8/2015 | Bhatia et al. |
| 2015/0246072 | A1 | 9/2015 | Bhatia et al. |
| 2015/0366655 | A1 | 12/2015 | Tumey et al. |
| 2016/0115457 | A1 | 4/2016 | Kim et al. |
| 2016/0122723 | A1 | 5/2016 | Retting et al. |
| 2017/0130192 | A1 | 5/2017 | Retting et al. |
| 2017/0136147 | A1 | 5/2017 | Tumey et al. |
| 2017/0218228 | A1 | 8/2017 | Jose et al. |
| 2023/0372637 | A1 | 11/2023 | Yoo et al. |

FOREIGN PATENT DOCUMENTS

| | | | | |
|---|---|---|---|---|
| WO | 2008124126 | | 10/2008 | |
| WO | 2008153968 | | 12/2008 | |
| WO | WO-2010030964 | A2 * | 3/2010 | ......... A61L 27/3886 |

OTHER PUBLICATIONS

International Search Report corresponding to International Application No. PCT/US2011/020551, Date of Mailing: May 25, 2011, 12 pages.

Pardo et al., "Characterization of Patterned Self-Assembled Monolayers and Protein Arrays Generated by the Ink-Jet Method", Langmuir, 2003, vol. 19, pp. 1462-1466.

Wilson et al., "Cell and Organ Printing 1: Protein and Cell Printers", The Anatomical Record Part A, 272A, 2003, pp. 491-496.

Supplementary European Search Report, EP11732221, mailed Jun. 5, 2013.

International Search Report and Written Opinion, PCT/US12/27731, mailed Jul. 13, 2012.

Supplementary European Search Report and Opinion, EP 12754610, mailed Aug. 4, 2014.

Bender et al., "Development of a novel delivery device for in situ bioprinting of the skin", Termis-Americas 2010 Orlando Conference, Dec. 5, 2010, 1 page.

Binder et al., "Drop-on-demand inkjet bioprinting: a primer", Gene Therapy and Regulation, Mar. 1, 2011, 6(1): 33-49.

Skardal et al., "Bioprinted amniotic fluid-derived stem cells accelerate healing of large skin wounds", Stem Cells Translational Medicine, 2012, 1: 792-802.

Fox, "Inkjet-like device 'prints' cells right over burns", reuters.com/articles/2010/04/08/us-wounds-printer-idUSTRE63657520100408, Retrieved from internet Jun. 8, 2015, 1 page.

Emspak, "Desktop printer technology used to lay down regenerated skin cells to treat burns in mice", Scientific American, Jun. 17. 2010, 3 pages, http://www.scientificamerican.com/article/desktop-printer-technology-lay-down-cells/.

Binder KK. Doctoral Dissertation: In situ bioprinting of the skin. Wake Forest University Graduate School of Arts and Sciences, Molecular Genetics and Genomics, May 2011; 463 pp.

Binder KW et al. Poster presentation, "In situ bioprinting of the skin for burns." 2009 Tissue Engineering and Regenerative Medicine International Society World Congress, dated Aug. 31-Sep. 3, 2009, 9 pp.

(56) References Cited

OTHER PUBLICATIONS

Notice of Preliminary Rejection, Korean Patent Application No. 10-2012-7020050, mailed Feb. 5, 2017.
Notice of Preliminary Rejection, Korean Patent Application No. 10-2013-7025987, dated May 18, 2018.
Binder, K., et al., "In Situ Bioprinting of the Skin for Reconstruction", Conference paper: 2010 American Academy of Pediatrics National Conference and Exhibition, Oct. 2010 (Abstract).

* cited by examiner

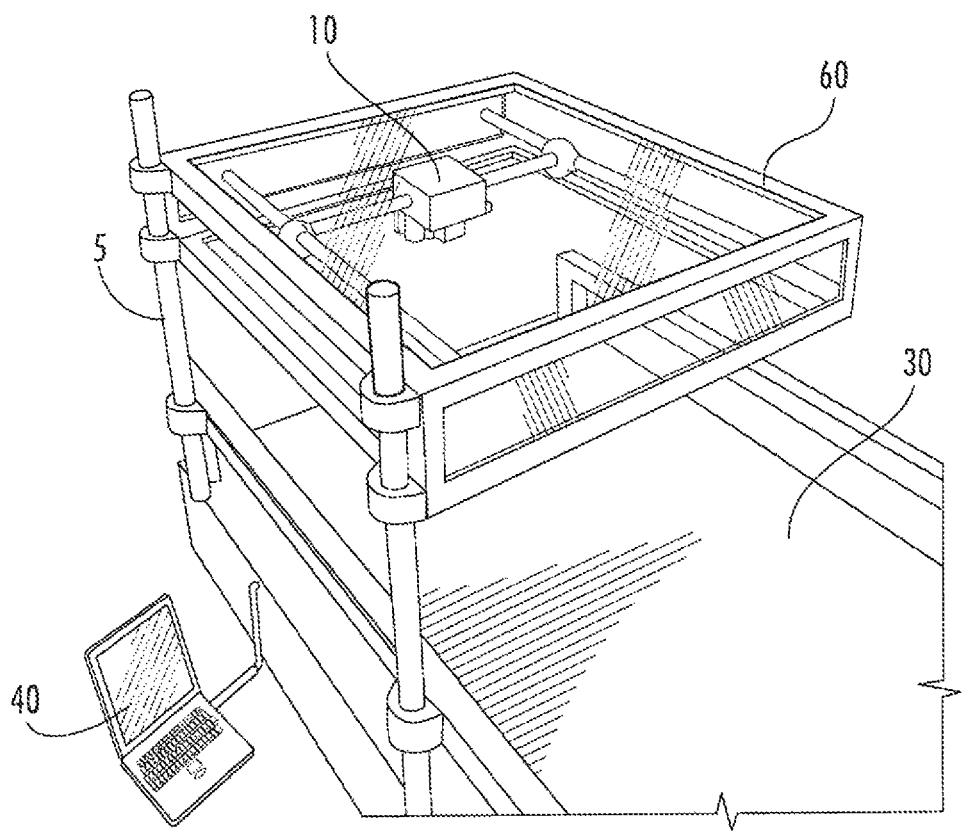
FIG. 6
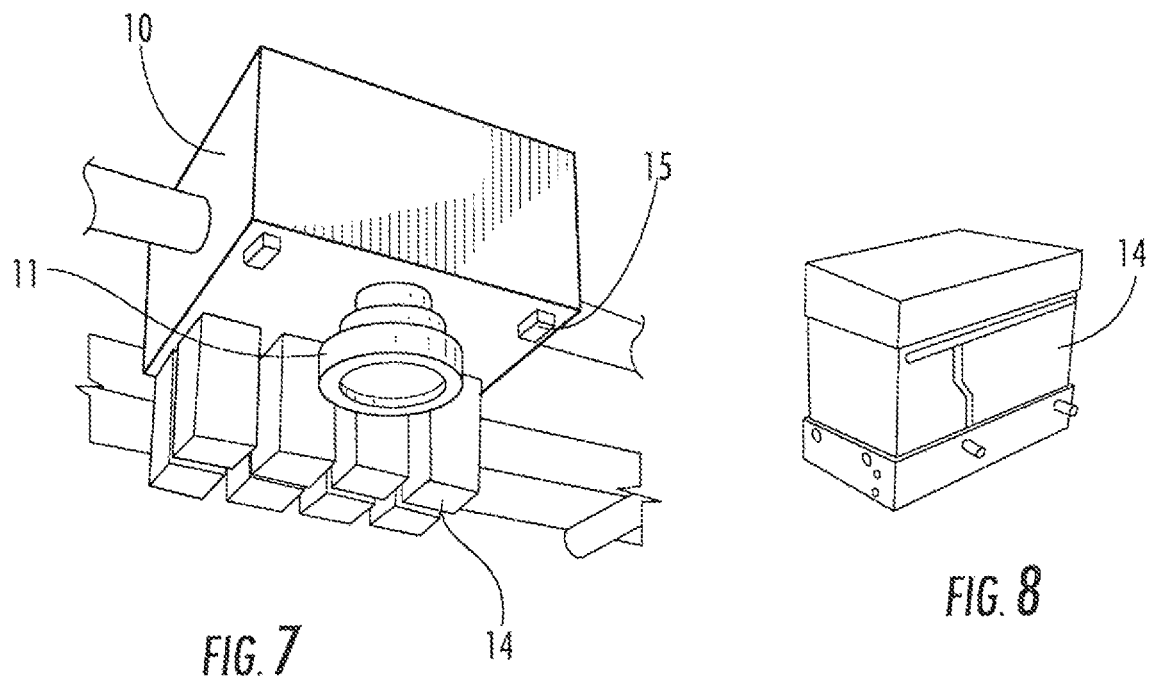
FIG. 7
FIG. 8

DELIVERY SYSTEM

RELATED APPLICATIONS

This application is a continuation of U.S. patent application Ser. No. 12/986,812, filed Jan. 7, 2011 which claims the benefit under 35 U.S.C. 119(e) of U.S. Provisional Patent Application Ser. No. 61/293,481, filed Jan. 8, 2010, the disclosures of which are incorporated herein by reference in their entireties

STATEMENT OF GOVERNMENT SUPPORT

This work was supported by grant W81XWH-08-2-0032 from the Armed Forces Institute for Regenerative Medicine. The U.S. Government has certain rights in this invention.

FIELD OF THE INVENTION

The present invention concerns the in situ delivery of viable cells onto a subject.

BACKGROUND OF THE INVENTION

In the United States, the mortality rate for burns is approximately 4.9% and increases dramatically with increasing total body surface area (TBSA) burned. The gold standard of treatment is the split-thickness autograft, but this technique requires injuring one or more sites of undamaged skin. Other treatment techniques include silver sulfadiazine, INTEGRA® (Johnson and Johnson, Hamburg, Germany; Integra Life Sciences Corporation, NJ). BIOBRANE® (Dow Hickam/Bertek Pharmaceuticals, Sugar Land, TX), TRANSCYTE® (Advanced Tissue Sciences, Inc., La Jolla, CA), and allogeneic cells.

Large-scale manufacturing processes necessitate production of standard sizes of skin substitutes, but these standard-sized products cannot adequately cover irregular wounds. In addition, nearly all of these techniques require multiple surgical procedures, and are not ideal for large body surface area burns.

Allogeneic cell therapy can eliminate the need for autologous cell culture. Current delivery techniques include spraying cells onto the patient or seeding a scaffold with cells before implantation. Cell spraying has been used to treat burns with autologous fibroblasts and keratinocytes, but the delivery precision of current spraying technology is low.

The ideal skin substitute possesses the following qualities: (1) it adheres intimately to the wound bed, especially for irregular surfaces; (2) it provides a non-antigenic microbial barrier: (3) it participates in normal host repair mechanisms; (4) it maintains elasticity and long-term durability; (5) it displays long-term mechanical and cosmetic function comparable to split-thickness autografts; (6) it requires a single surgical procedure; (7) it is inexpensive; (8) it has an indefinite shelf life; and (9) it has minimal storage requirements.

New treatments are needed that better address the needs of burn wound patients, as well as patient having other wounds and tissue injury or disease.

SUMMARY OF THE INVENTION

Provided herein is a delivery system, including: (a) an optical sensor configured to detect data used to create a map of a bodily surface; and (1)) a printer operatively associated with the optical sensor and configured to deliver cells and/or compositions to the bodily surface based upon the map. The sensor and printer can be associated with one another by connection of each to a common support or frame, to which may also be connected a subject support (e.g., a bed) to place a subject in a position for scanning of the subject's bodily surface. In some embodiments, the optical sensor includes a three-dimensional scanner. In some embodiments, the optical sensor includes an infrared detector. In some embodiments, the optical sensor is a laser scanner.

In some embodiments, the system further includes: (c) a three-dimensional plotter operatively connected with the optical sensor; and (d) a controller operatively connected with the printer.

In some embodiments, the printer includes a cartridge loaded with a composition (e.g., a composition including cells, support compounds, growth factors, combinations thereof, etc.). In some embodiments, the cartridge includes a plurality of printheads, and wherein the cartridge is in fluid communication with the plurality of printheads. In some embodiments, the printheads include nozzles configured for pressure-based delivery of cells and/or compositions.

Methods of forming a tissue on a bodily surface of a patient in need thereof are also provided, including: (a) scanning the bodily surface to obtain the three dimensional coordinates thereof; and then (b) printing viable cells on the bodily surface of the patient based upon the coordinates to thereby form the tissue. In some embodiments, the printing step is performed two or more times in sequence to make a tissue having multiple layers.

Also provided are methods of processing bodily surface data obtained from a three dimensional optical detector to provide a path to a printer operatively associated to the optical detector, the methods including: interpreting the bodily surface data from the optical detector to form a model of the bodily surface; transforming the model into a negative mold of the bodily surface, which mold is split into a plurality of Z-axis layers, which layers correspond to one or more tissue layers; and overlaying each of the tissue layers with a series of lines which cover the bodily surface, wherein the lines provide a path for the printer. In some embodiments, the methods further include the step of obtaining the bodily surface data by scanning with a three-dimensional optical sensor. In some embodiments, the bodily surface data is wound surface data (e.g., skin wound surface data).

Further provided are systems for processing data of a bodily surface obtained from a three dimensional optical detector to provide a path to a printer operatively associated to the optical detector, the system including: means for interpreting the bodily surface data from the optical detector to form a model of the bodily surface; means for transforming the model into a negative mold of the bodily surface, which mold is split into a plurality of Z-axis layers, which layers correspond to one or more tissue layers; and means for overlaying each of the tissue layers with a series of lines which cover the bodily surface, wherein the lines provide a path for the printer. Some embodiments further include means for obtaining the bodily surface data. In some embodiments, the bodily surface data is wound surface data (e.g., skin wound surface data).

Computer program products are also provided for processing data of a bodily surface obtained from a three dimensional optical detector to provide a path to a printer operatively associated to the optical detector, the computer program product including a computer readable medium having computer readable program code embodied therein, the computer readable program code including: computer readable program code which interprets the bodily surface data from the optical detector to form a model of the bodily surface; computer readable program code which transforms the model into a negative mold of the bodily surface, which mold is split into a plurality of Z-axis layers, which layers correspond to one or more tissue layers; and computer readable program code which overlays each of the tissue layers with a series of lines which cover the bodily surface, wherein the lines provide a path for the printer. In some embodiments, the bodily surface data is wound surface data (e.g., skin wound surface data).

The foregoing and other objects and aspects of the present invention are explained in greater detail in the drawings herein and the specification set forth below.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 6. Alternative embodiment of delivery system (5) having an attached computer (40) and a cover (60) over the printer support (10). The system (5) is attached to a table (30).

FIG. 7. Cutout view of printer support (10) having a camera (11), infrared sensors (15), and a plurality of printer cartridges (14).

FIG. 8. Exploded view of a printer cartridge (14).

DETAILED DESCRIPTION OF THE PREFERRED EMBODIMENTS

Provided herein and further described below are systems, compositions, devices and methods useful for the delivery of cells and tissues onto a subject in need thereof. In some embodiments, a cartridge based cell delivery system including a printer is provided, which printer is operatively associated with a scanner.

The disclosures of all United States patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

Unless otherwise defined, all terms (including technical and scientific terms) used herein have the same meaning as commonly understood by one of ordinary skill in the relevant art. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The present invention is described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Figure 1:
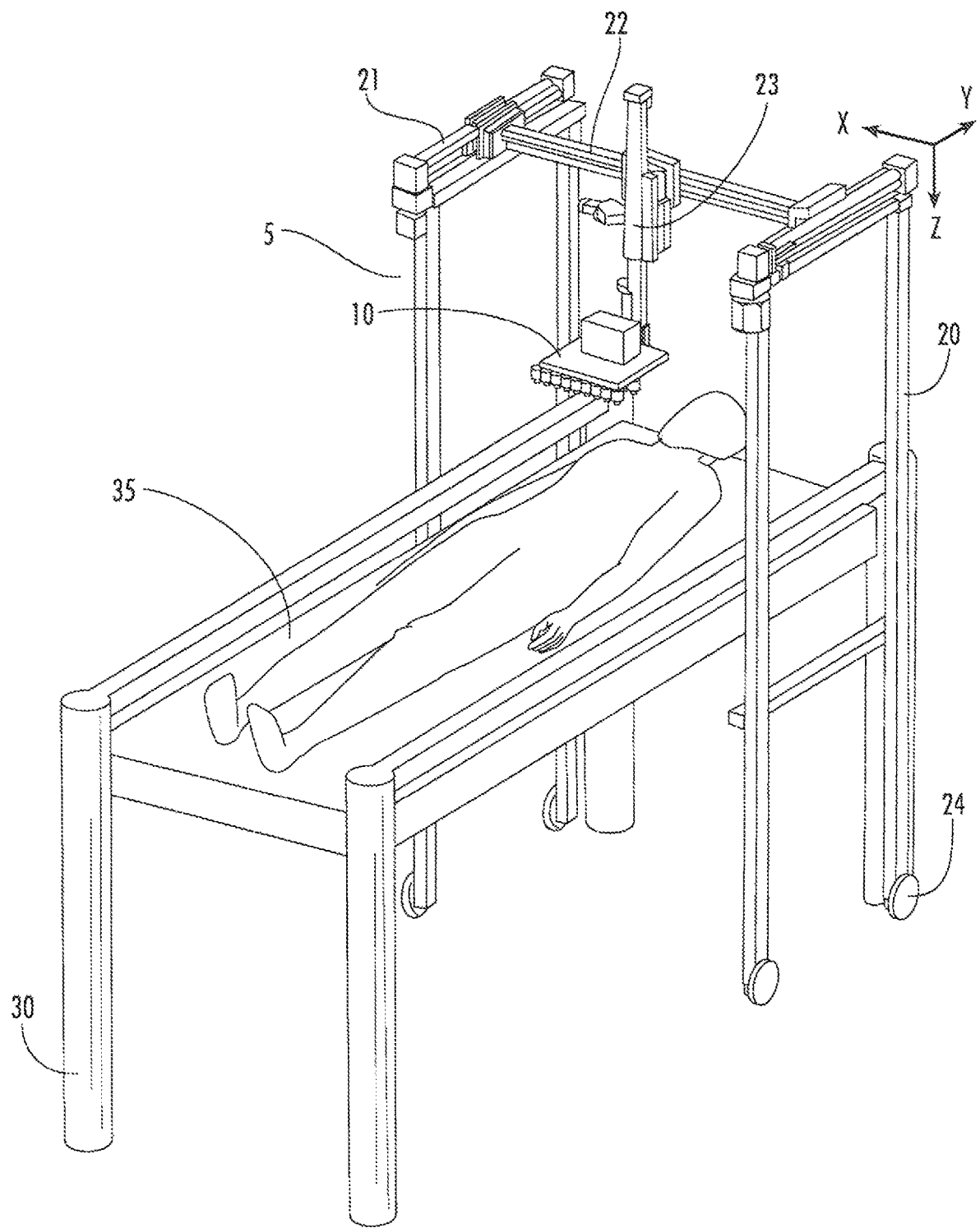
FIG. 1. Perspective view of delivery system (5) having a printer support (10). This portable embodiment has wheels (24), and is positioned over a subject lying on a table (30) having a bed (35). The printer support is operatively connected to members (23, 22, 21) configured to allow the printer support (10) to be moveable about the Z axis (member 23), the X axis (member 22), and the Y axis (member 21).

As illustrated in FIG. 1, in some embodiments a delivery system (5) is provided which includes a printer support (10) thereon. In some embodiments, the delivery system may be provided on wheels (24) for portability. The delivery system (5) may be positioned over a subject lying on a table (30) having a bed (35) when in use. In some embodiments, a locking mechanism may be provided to lock the delivery system (5) in place relative to the table (30) or bed (35).

The printer support (10) according to some embodiments is operatively connected to members (23, 22, 21) configured to allow the printer support (10) to be moveable about the Z axis (member 23), the X axis (member 22), and the Y axis (member 21).

Figure 2:
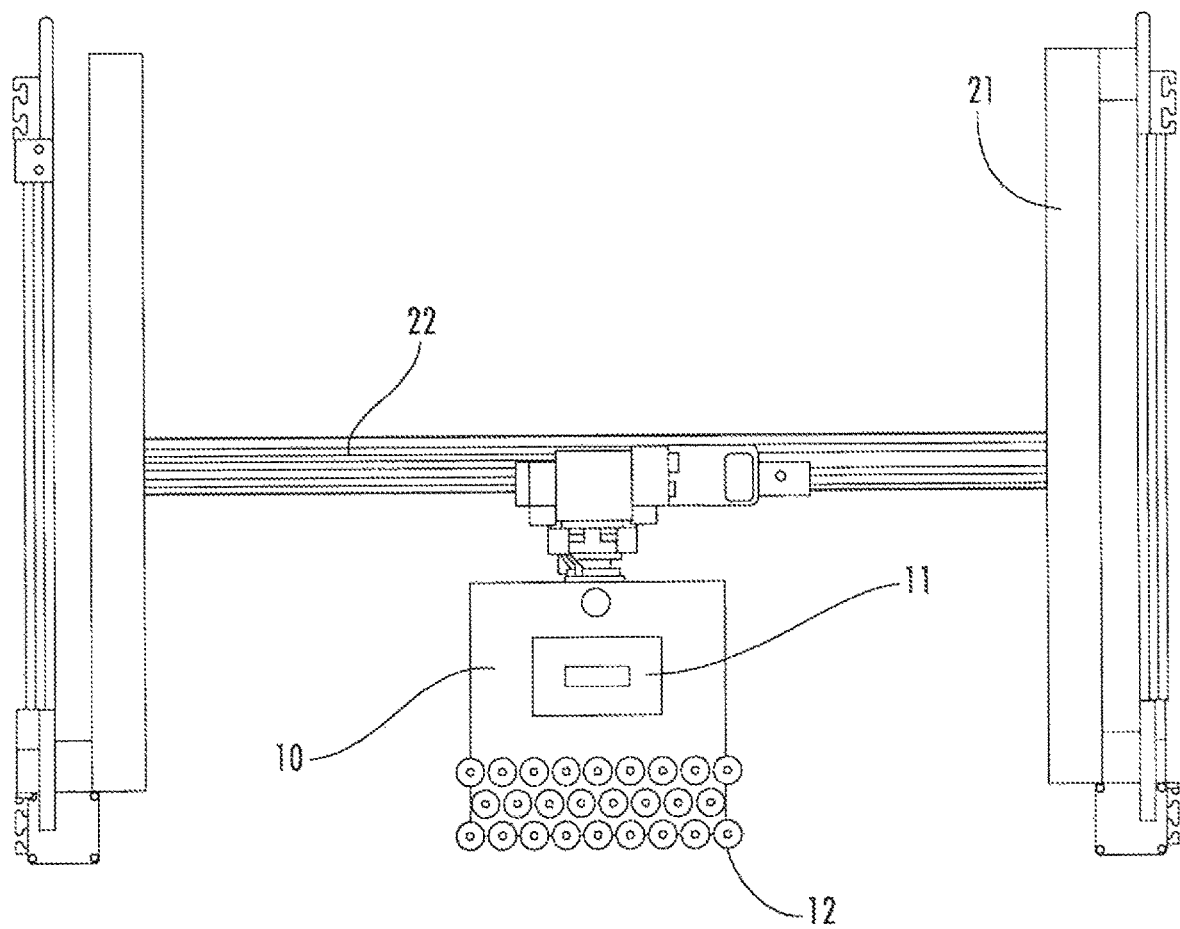
FIG. 2. Bottom view of printer support (10) having optical sensor (11) and a plurality of printheads (12).

As illustrated in FIG. 2, in some embodiments the printer support (10) includes an optical sensor (11) and a plurality of printheads (12). In other embodiments, the printer support includes a plurality of printheads (12), but the optical sensor (11) is provided on a separate support (not shown).

Figure 3:
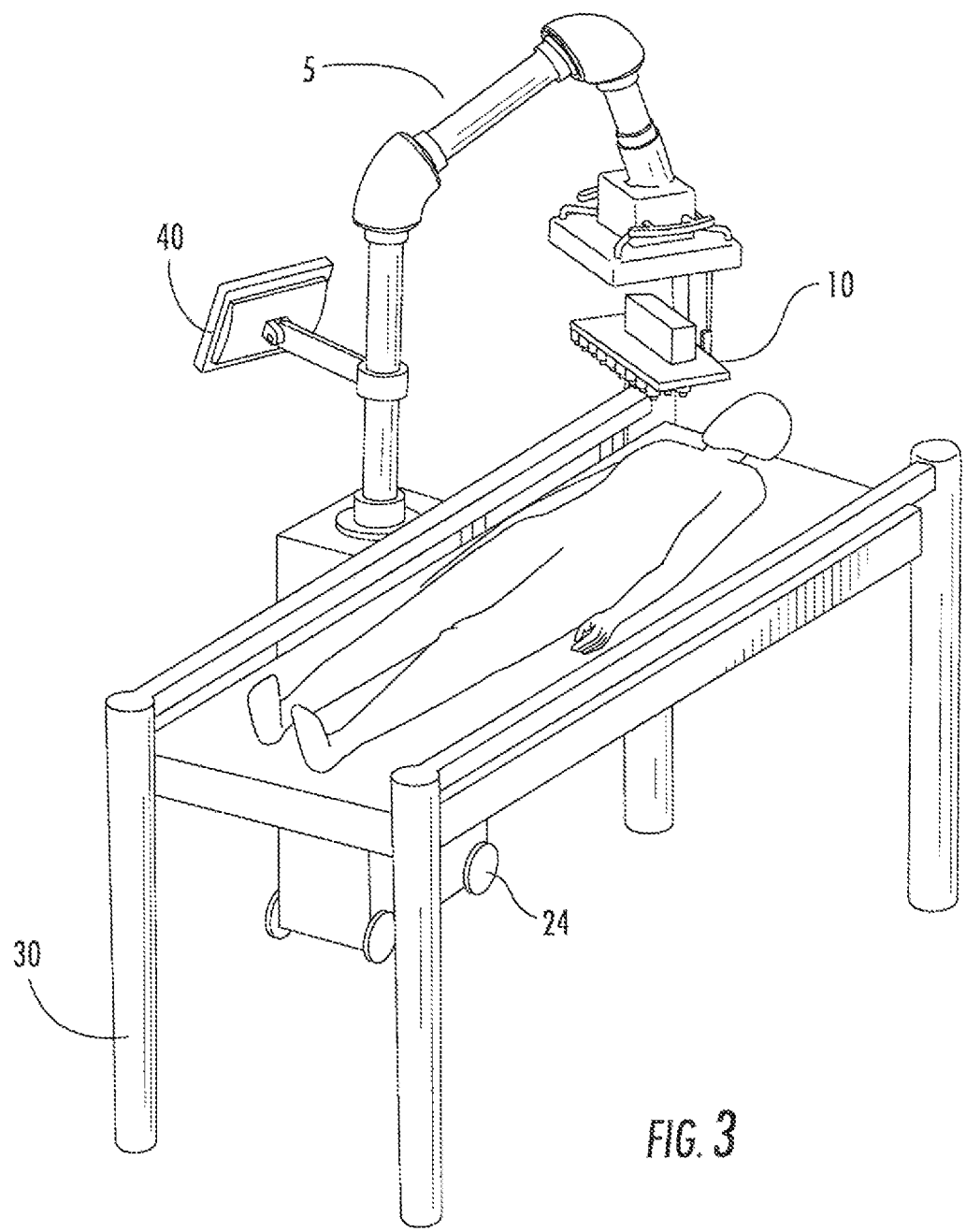
FIG. 3. Alternative embodiment of portable delivery system (5) having an attached computer (40), positioned over a subject lying on a table (30).
Figure 4:
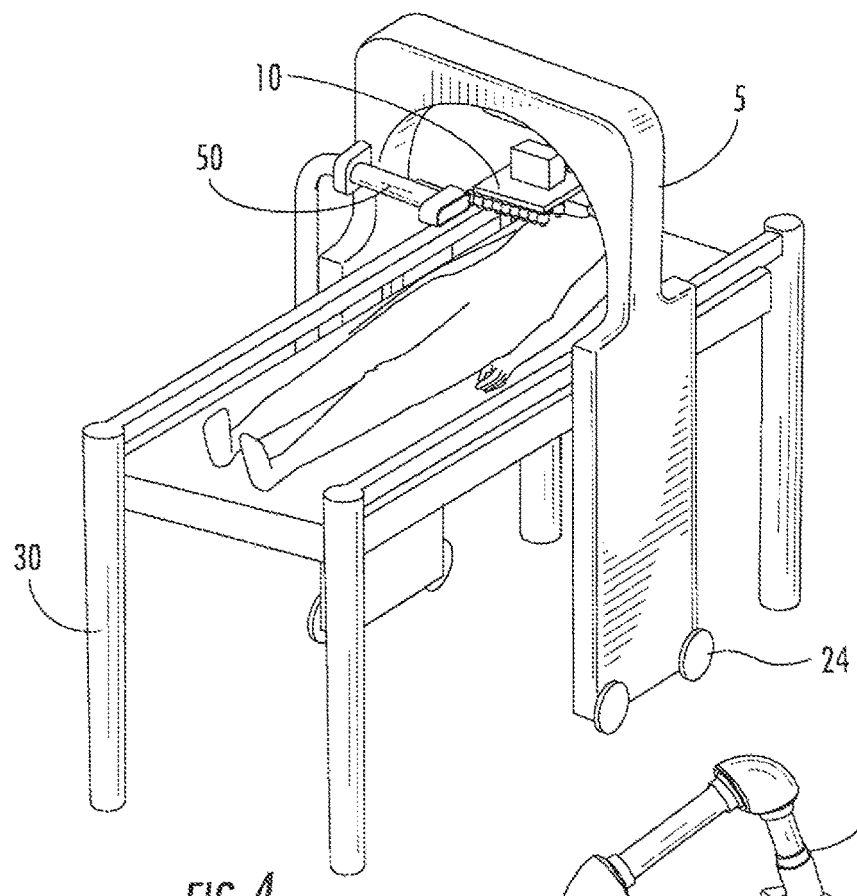
FIG. 4. Alternative embodiment of portable delivery system (5) having an attached light (50), positioned over a subject lying on a table (30)
Figure 5:
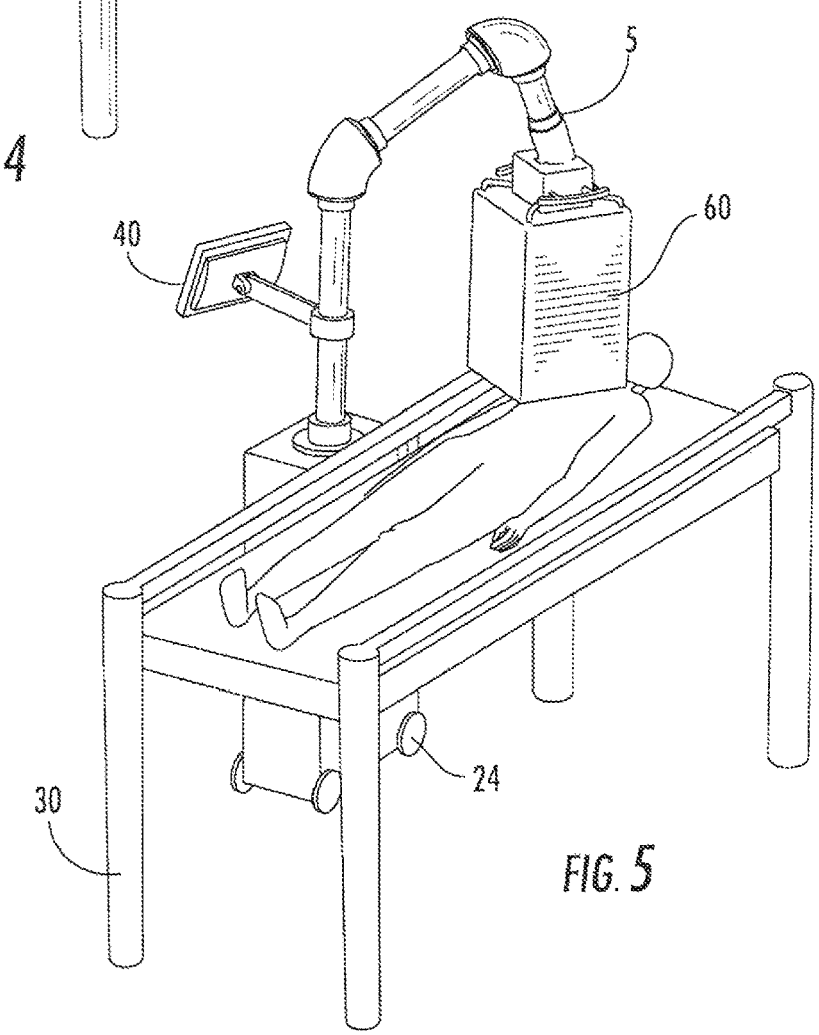
FIG. 5. Alternative embodiment of portable delivery system (5) having an attached computer (40) and a cover (60) over the printer support (10), positioned over a subject lying on a table (30).

Some alternative embodiments of the delivery system (5) are illustrated in FIGS. 3-6. FIG. 3 illustrates an embodiment of the delivery system having an attached computer (40), positioned over a subject lying on a table (30). FIG. 4 illustrates another embodiment, and includes an attached light (50), positioned over a subject lying on a table (30). FIG. 5 illustrates an embodiment having an attached computer (40) and a cover (60) over the printer support (10), positioned over a subject lying on a table (30). FIG. 6 illustrates an embodiment of a delivery system (5) having an attached computer (40) and a cover (60) over the printer support (10). The system (5) is attached to a table (30).

FIG. 7 illustrates an embodiment of a printer support (10) having a camera (11), infrared sensors (15), and a plurality of printer cartridges (14).

An aspect of the present invention is a method of treating a wound (e.g., burns, abrasions, lacerations, incisions, pressure sores, puncture wounds, penetration wounds, gunshot wounds, crushing injuries, etc.) in a subject in need thereof, in which cells and/or compositions are applied thereto in an amount effective to treat the wound.

Examples of wounds that can be treated with the present invention include burn wounds. Burn wounds are tissue injuries that can result from heat, chemicals, sunlight, electricity, radiation, etc. Burns caused by heat, or thermal burns, are the most common. Chemical burns resemble thermal burns. Though burn wounds tend to occur most often on the skin, other body structures may be affected. For example, a severe burn may penetrate down to the fat, muscle or bone. In some embodiments, cells corresponding to one or more of these tissues may be delivered onto the wound site, e.g., in a layer-by-layer application that mimics the natural tissues.

Wounds may be characterized by the depth of injury as known in the art. For example, the degree of a burn is characterized as first, second or third depending on the depth of the tissues injured. In a first-degree burn, only the top layer of skin (the epidermis) is damaged. In second-degree burns, the middle layer of skin (the dermis) is damaged. Finally, in a third-degree burn, the most severe type, the damage is deep enough to affect the inner (fat) layer of the skin. Similarly, pressure sores of the skin are characterized as stage I (red, unbroken skin, erythema does not fade with release of pressure), stage II (disrupted epidermis, often with invasion into the dermis), stage III (injury of the dermis), and stage IV (subcutaneous tissue is exposed).

In pressure sore wounds, pressure-induced constriction of local capillaries results in ischemia in the affected skin. Similarly, a burn wound is ischemic due to associated capillary thrombosis. A diabetic ulcer is another example of a poorly perfused wound. For these types of wounds, where blood is not readily available to aid in the normal course of wound healing, in some embodiments dead and/or injured tissue is removed (debridement) prior to application of the cells as provided herein.

In some embodiments, compositions may include an antimicrobial agent to decrease the risk of infection. In some embodiments, compositions may include analgesics or anesthetics for pain relief, surfactants, anti-inflammatory agents, etc. See, e.g., U.S. Pat. No. 6,562,326 to Miller. Methods of attenuating swelling, such as treatment with cold (e.g., cool water, ice, etc.) and elevation of the affected area, may also be used.

According to some embodiments, the device may be used for both open wounds and closed wounds. In the case of closed wounds, the scanner and/or delivery device may be allowed access to the wound site through surgical means, inclusive of endoscopic procedures.

In some embodiments, reapplication of the disclosed cells and/or compositions may be performed as needed. Cleansing to remove bacteria and debridement to remove necrotic debris may also be warranted during the course of treatment. Application of a moisturizing cream or ointment may be used to soften wound eschar in order to assist in debridement.

A. Printer.

In some embodiments, cells, proteins, support materials, combinations thereof, etc., are delivered with a printer. "Printing" as used herein refers to the delivery of droplets of cells and/or compositions with small volumes, e.g., from 0.5 to 500 microLiters, or 5 to 100 microLiters, or from 10 to 75 microLiters per droplet. In some embodiments, droplets have a volume ranging from 0.5 to 500 picoLiters, or 5 to 100 picoLiters, or from 10 to 75 picoLiters per droplet. Printing may be performed by, e.g., using standard printers with print heads that are modified as described herein. The "printhead" is the device in an inkjet printer that sprays droplets (e.g., ink, or as used herein, cells and/or compositions).

In some embodiments, printing can provide a precise delivery of cells to a resolution of approximately 5, 10, 20, 30, 40, 50, 60, 70, 80, 90, 100, or 200 µm. Printing can also deliver specific cells to specific target sites using a layer-by-layer fabrication. Such layer-by-layer fabrication may in some embodiments be performed in situ on a subject in need thereof, and involve multiple cell types arranged with precision. This is in contrast to cell seeding or spraying techniques, in which cells are randomly applied over a large area.

A "cartridge" as used herein refers to a vessel or reservoir in which cells and/or compositions may be held, and which is in fluid communication with one or more nozzles in one or more printheads. The cartridge may include the reservoir and delivery mechanism in a single unit, as in a traditional inkjet cartridge, or the reservoir and delivery mechanism may be in separate units but connected such that they are in fluid communication (e.g., through the use of tubing).

In some embodiments, one or more cell types and/or compositions are loaded into an individual cartridge. "Compositions" may include cells, carriers, support materials, macromolecules such as proteins, cytokines, growth factors, etc., or any combination thereof. Compositions may also include oxygen generating biomaterials. See PCT Publication WO 2008/124126.

In some embodiments, each cartridge is configured to connect to multiple nozzles and/or printheads, in contrast to standard inkjet printing in which one printhead is connected to one cartridge. This allows arbitrary printhead configurations that can conform to the needs of the treatment. It also increases the throughput of the system and provides a rapid method of sterilization by attaching a cartridge of cleaning fluid to the printheads.

In some embodiments, the printheads contain pressure-based nozzles. A pressure-based delivery system according to some embodiments allows the printer to remain a safe distance above the patient and to accommodate a variety of body types. As used herein, a "pressure-based" delivery system uses three components: the pressure source, material reservoirs, and delivery mechanism. In some embodiments, the delivery mechanism is a series of voltage operated inkjet valves. The pressure source is operatively connected to the reservoir, which is in fluid communication with the delivery mechanism. In some embodiments, a gas (e.g., air, air plus 5% $CO_2$, etc.) is pumped into empty space in the reservoir by the pressure source, which in turn drives the material in the reservoir (cells and/or compositions) into the delivery mechanism.

This pressure-based system may be preferable in some embodiments as compared to inkjet cartridges in the context of in situ priming because it separates the reservoir and delivery mechanism. A traditional inkjet cartridge includes the reservoir and delivery mechanism in a single unit. If either the reservoir or delivery mechanism fails, then the entire unit fails. Furthermore, inkjet cartridges must be filled and sealed prior to printing. If the inkjet cartridge is filled with cells, failure of the cartridge means the loss of all cells contained in that cartridge. The pressure-based delivery system solves both of these issues. The reservoir and delivery mechanism can be replaced individually in the case of failure of either component. Material is only pumped to the delivery mechanism when it is needed, so failure of the delivery mechanism does not result in the loss of all material in the reservoir.

In addition, in some embodiments the pressure-based system can provide a method of detecting and clearing clogged valves. By placing a pressure sensor at the end of the valve, the delivery pressure can be compared to the applied pressure. If the difference between the two pressures is larger than a certain threshold, then the valve is clogged. Redirecting the output of the valve to a waste reservoir and applying a large burst of pressure may be used to try and clear the valve. If the clearing process fails, then the system will detect this and can continue printing without using that valve.

In some embodiments, the printer includes a two-dimensional (X-Y) or three-dimensional (X-Y-Z) plotter (e.g., driven by step motors). In some embodiments, the print head is equipped with a DC solenoid inkjet valve. In some embodiments, one or more, or several, reservoirs for loading cells is connected to the inkjet valve. In some embodiments, the cells and/or compositions may be supplied from the reservoirs to the valve or nozzle by air pressure. In some embodiments, the print head may be mounted on an X-Y-Z plotter to allow precise deposition of cells onto a scaffold. Positioning of the XYZ plotter under the print head may be controlled via a controller. In some embodiments, the controller acquires the positioning information from software loaded on a computer. In some embodiments, the software converts the image of the target to a four-byte protocol, which is used to activate specific inkjet valves and coordinate the X-Y-Z position.

Cells may be printed in the form of a composition that contains a carrier. The cells may be provided in the form of a suspension, solution, or any suitable form. The carrier may be a solid or a liquid, or both (e.g., a gel). In some embodiments, the cells are provided as a suspension in the carrier to reduce clumping of the cells. Support compounds, growth factors, etc., may be included in compositions having cells and/or may be included in compositions without cells (but may include a suitable carrier), as desired.

Suitable gels include, but are not limited to, agars, collagen, fibrin, hyaluronic acid, hydrogels, etc. Besides gels, other support compounds may also be utilized in the present invention. Extracellular matrix analogs, for example, may be combined with support gels to optimize or functionalize the gel. One or more growth factors may also be included. In some embodiments a temperative sensitive gel may be used. Examples of temperature sensitive gels include thermaosensitive hydrogels and thermosensitive polymer gels (e.g., a poloxamer such as Pluronic® F-127 (BASF corporation, Mont Olive, New Jersey)). See also U.S. Pat. Nos. 6,201,065, 6,482,435.

Examples of suitable liquid carriers include, but are not limited to, water, ionic buffer solutions (e.g., phosphate buffer solution, citrate buffer solution, etc.), liquid media (e.g., modified Eagle's medium ("MEM"), Hanks' Balanced Salts, etc.), and so forth. The use of a liquid or gel carrier in the cell composition may in some embodiments ensure adequate hydration and minimize evaporation of the cells after printing.

Cells may also be transfected (e.g., with a specific gene) with material of interest. Useful genetic material may be, for example, genetic sequences that are capable of reducing or eliminating an immune response in the host. For example, the expression of cell surface antigens such as class I and class II histocompatibility antigens can be suppressed. This would allow the transplanted cells to have a reduced chance of rejection by the host. Cells may also be transfected with a gene encoding one or more growth factors. According to some embodiments, cells may be transfected during the printing process. See PCT publication WO 2008/153968 to Xu et al.

The present invention includes the printing of tissues by the appropriate combination of cell and support material, or two or three or more different cell types typically found in a common tissue, preferably along with appropriate support compound or compounds, and optionally with one or more appropriate growth factors. Cells, support compounds, and growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degradable support material), and some of the ingredients may be printed in the form of a second pattern (e.g., cells in a pattern different from the support, or two different cell types in a different pattern). Again, the particular combination and manner of printing will depend upon the particular tissue construct desired.

In alternative embodiments in which increased delivery precision is desired, the printer uses thermal or piezoelectric printheads and/or inkjet cartridges for increased delivery precision. Methods and compositions for the inkjet printing of viable cells are known and described in, for example, U.S. Pat. No. 7,051,654 to Boland et al.; Wilson et al. (2003) The Anatomical Record Part A 272A: 491-496.

In some embodiments, cells/compositions are printed with a modified inkjet printer. Modifications may include, but are not limited to, means to control the temperature, humidity, shear force, speed of printing, and firing frequency, by modifications of, e.g., the printer driver software and/or the physical makeup of the printer. See, e.g., Pardo et al. (2003) *Langmuir* 19:1462-1466; U.S. Pat. No. 7,051,654 to Boland et al. Not every modification suggested in these references will be suitable to a given application, as will be appreciated by those skilled in the art. For example, in some embodiments, printers are not modified by using new gear mount pillars with closer tolerances by adding a horizontal support, changing the transistor in the circuit to one with higher amplification, and reentering the horizontal position encoder. Also, in some embodiments, printer software is not modified to lower the resistive voltages to avoid heating of the solutions above 37° C.

In some embodiments, printers (e.g., the commercial printers HP695C and HP550C) may be modified as follows. The printer top cover may be removed and the sensor for the cover disabled. The paper feeding mechanism may be disabled to allow printing of cells onto solid substrates (e.g., scaffolds). The ink absorbing pads (which are on the right side of the HP695C and HP550C printers) may be removed (e.g., to avoid the pads contaminating the bottom of the print cartridges during the printing process). To offer the capability of the printer to print 3D constructs, a customized Z-axis module with a controlled elevator chamber may be added.

In some embodiments, the printer is a thermal bubble inkjet printer. In general, in a thermal bubble inkjet printer, resistors create heat in the print head, which vaporizes ink to create a bubble. As the bubble expands, some of the ink is pushed out of a nozzle onto the paper. A vacuum is created when the bubble collapses, which pulls more ink into the print head from the cartridge. In the present invention, the ink is replaced with, e.g., cells and/or compositions of interest (e.g., cells in a liquid carrier), and the paper is replaced with a suitable substrate, e.g., an agar or collagen coated substrate, or a suitable scaffold. See, e.g., U.S. Pat. No. 6,537,567 to Niklasen et al.

In other embodiments, cells are printed using a piezoelectric crystal vibration print head. In general, a piezoelectric crystal receives an electric charge that causes it to vibrate, forcing ink out of the nozzle, and pulling more ink into the reservoir. In the present invention, the ink is replaced with, e.g., cells and/or compositions of interest. Compared with the thermal inkjet printing, the piezo-based inkjet printing usually requires more power and higher vibration frequencies. Typical commercial piezo-printers use frequencies up to 30 kHz and power sources ranging from 12 to 100 Watts. Therefore, in some embodiments a piezoelectric crystal vibration print head is used, with a vibrating frequency of 1, 5, 10 or 15, to 20, 25, 30, or 35 or more kHz, and power sources from 5, 10, 20, 50, 100, 120, or 150, to 200, 250, 300, 350, or 375 or more Watts.

The cells may also be printed by other means, such as the methods and compositions for forming three-dimensional structures by deposition of viable cells described in U.S. Pat. No. 6,986,739 to Warren et al.

In some embodiments, the print head nozzles are each independently between 0.05 and 200 μm in diameter, or between 0.5 and 100 μm in diameter, or between 10 and 70 μm, or between 20 and 60 μm in diameter. In further embodiments, the nozzles are each independently about 40 or 50 μm in diameter. In still further embodiments, the nozzles are each independently between 0.1 or 0.5 and 2 or 3 mm. A plurality of nozzles with the same or different diameters may be provided. A more narrow nozzle may give greater precision delivery but low throughput, and vice versa. These may be provided according to cell type and/or precision desired. Though in some embodiments the nozzles have a circular opening, other suitable shapes may be used, e.g., oval, square, rectangle, etc., without departing from the spirit of the invention.

In some embodiments, the cells/compositions are formulated to provide an encapsulated form upon printing. The encapsulation of cells in permeable capsules is known, and described in, for example, U.S. Pat. No. 6,783,964. For example, the cells may be encapsulated in a microcapsule of from 50 or 100 μm to 1 or 2 mm in diameter that includes an internal cell-containing core of polysaccharide gum surrounded by a semi permeable membrane; a microcapsule that includes alginate in combination with polylysine, polyornithine, and combinations thereof. Other suitable encapsulating materials include, but are not limited to, those described in U.S. Pat. No. 5,702,444.

"Encapsulated" cells are cells or small clusters of cells or tissue that are surrounded by a selective membrane laminate that allows passage of oxygen and other required metabolites, releases certain cell secretions (e.g., insulin), but limits the transport of the larger agents of the host's immune system to prevent immune rejection. Encapsulation may be useful for, e.g., the delivery of cells and/or tissues containing xenogeneic or allogeneic cells while reducing the risk of immune rejection in a host. This may be useful, e.g., to treat diseases due to inadequate or loss or secretory cell function, or ailments that would benefit from the addition of certain secretory cells. "Microencapsulation" of cells is where one, two, three or several cells are encapsulated. In some embodiments, each membrane encapsulates 10 cells or less, preferably 5 cells or less, of at least 50, 70, 80, 90 or 95% or more of the printed cells.

In some embodiments, two or more layers may be separately applied, with subsequent layers applied to the top surface of previous layers. The layers can, in one embodiment, fuse or otherwise combine following application or, alternatively, remain substantially separate and divided following application to the subject.

The thickness of a printed layer (e.g., cell layer, support layer, etc.) may generally vary depending on the desired application. For example, in some embodiments, the thickness of a layer containing cells is from about 2 micrometers to about 3 millimeters, and in some embodiments, from about 20 micrometers to about 100 micrometers. Further, as indicated above, support compounds, such as gels, may be used to facilitate the survival of printed cells.

"Support compounds" which may be included in compositions may be any naturally occurring or synthetic support compound, including combinations thereof, suitable for the particular tissue being printed. In general, the support compound is preferably physiologically acceptable or biocompatible. Suitable examples include, but are not limited to, alginate, collagen (including collagen VI), elastin, keratin, fibronectin, proteoglycans, glycoproteins, polylactide, polyethylene glycol, polycaprolactone, polycolide, polydioxanone, polyacrylates, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, and derivatives and copolymers thereof (see, e.g., U.S. Pat. Nos. 6,991,652 and 6,969,480) as well as inorganic materials such as glass such as bioactive glass, ceramic, silica, alumina, calcite, hydroxyapatite, calcium phosphate, bone, and combinations of all of the foregoing.

When printing certain types of two-dimensional or three-dimensional tissues or portions thereof, it is sometimes desired that any subsequent cell growth is substantially limited to a predefined region. Thus, to inhibit cell growth outside of this predefined region, compounds may be printed or otherwise applied to the print area that inhibit cell growth and thus form a boundary for the printed pattern. Some examples of suitable compounds for this purpose include, but are not limited to, agarose, poly (isopropyl N-polyacrylamide) gels, and so forth.

In one embodiment, for instance, this "boundary technique" may be employed to form a multi-layered, three-dimensional tube of cells, such as blood vessels. For example, a cell suspension may be mixed with a first gel ("Gel A") in one nozzle, while a second gel ("Gel B") is loaded into another nozzle. Gel A induces cell attachment and growth, while Gel B inhibits cell growth. To form a lube, Gel A and the cell suspension are printed in a circular pattern with a diameter and width corresponding to the diameter and wall thickness of the tube, e.g., from about 3 to about 10 millimeters in diameter and from about 0.5 to about 3 millimeters in wall thickness. The inner and outer patterns are lined by Gel B defining the borders of the cell growth. For example, a syringe containing Gel A and "CHO" cells and a syringe containing Gel B may be connected to the nozzle. Gel B is printed first and allowed to cool for about 1 to 5 minutes. Gel A and CHO cells are then printed on the agarose substrate. This process may be repeated for each layer.

B. Optical Detector.

In some embodiments, the area or areas of interest onto which cells and/or compositions are to be delivered is detected by an optical detector device to determine the two-dimensional and/or three-dimensional map of the area of interest. The optical detector is, in some embodiments, operatively associated with an attached cell delivery device, such that the cell delivery pattern may be optimized for in situ delivery of foe cells and/or compositions based upon such map.

"Map" as used herein refers to the two- and/or three-dimensional surface measurements, coordinates, and/or any other data that may represent the two- and/or three-dimensional surface of an area of interest (e.g., a wound). The map may be updated by scanning at any time, and/or in real time during delivery of cells and/or compositions.

As used herein, the "optical detector" may comprise one or more detectors that detect light at various wavelengths, e.g., visible light, infrared, ultraviolet, combinations thereof, etc. In some embodiments, both visible light and infrared light are detected.

In some embodiments, an optical detector such as a camera may be used to capture images that coincide with the surface measurements of the area of interest. In some embodiments, an image sensor is used to collect light reflected from an object and generate an image of the object. A mirror and lens system may be combined with the imaging device to focus the light reflected by the object onto the image sensor. The image sensor may be one of a charge coupled device (CCD) and a complementary metal oxide semiconductor (CMOS), typically arranged into an area array, although the invention is not so limited. The number of sensors, each representing a pixel (short for "picture element"), determine the resolution of the image taken. A pixel is the smallest unit that makes up a digital image, and can represent the shade and/or color of a portion of an image. The output of a set of image sensors may be encoded as a set of pixels to create a digital image. The digital image may be stored in a compressed format such as in a jpeg, tiff, and/or gif format, among others. The image may then be stored in a digital storage device and may be displayed on a monitor by a display application.

In some embodiments, the optical detector is a three dimensional scanner such as that described in U.S. Pat. No. 6,856,407 to Knighton et al. (incorporated by reference herein), in which depth data for a three-dimensional object may be calculated from an intensity difference resulting from an intensity gradient projected on the object capturing an intensity at a location on a surface in a single pixel of an image sensing array (ISA). The intensity may be convened into a measurement of distance to the location relative to a reference point independently of data from other pixels of the ISA and independent of lime of flight of light reflected from the location to the single pixel. A plurality of captures of the intensity at the location may be compared under different conditions to compensate for non-homogenous environments or surfaces.

In some embodiments, the optical detector is a three dimensional scanner as described in U.S. Patent Application Publication No. 2005/0237581 to Knighton et al. (incorporated by reference herein). The scanning device may be used to generate three dimensional representation of an area of interest. As used herein, three dimensional representations may be any type of digital modeling, abstraction and/or similar techniques that may utilize depth maps, polygon meshes, parametric solids, point clouds and similar data structures to create and store a three dimensional representation of the scanned object. The scanner may include a lens or set offenses to focus light on one or more image sensing arrays (ISA). In some embodiments, the ISAs may be a charged coupled device (CCD), complementary metal oxide semiconductor (CMOS) sensor, or similar imaging array. In some embodiments, lenses may be replaced by and/or supplemented with a reflector, light guide and/or similar article. By varying the focal settings, different aspects of the relief of an object may be brought into focus on an ISA. In some embodiments, an optical system having one or more optical elements distributes a same view of a target to a plurality of ISA's, each having a different focal range relative to the target.

Stereovision may also be used. Traditional stereovision methods estimate shape by establishing spatial correspondence of pixels in a pair of stereo images. A new concept called spacetime stereo has been developed, which extends the matching of stereo images into the time domain. By using both spatial and temporal appearance variations, it was shown that matching ambiguity could be reduced and accuracy could be increased. The shortcoming of spacetime stereo or any other stereo vision method is that matching of stereo images is time-consuming, therefore making it difficult to reconstruct high-resolution 3D shapes from stereo images in real time.

Further vision based surface mapping techniques may use structured light, which includes various coding methods and employs varying number of coded patterns. Unlike stereo vision methods, structured light methods usually use processing algorithms that are much simpler. Therefore, it becomes possible to achieve real-time performance, i.e., measurement and reconstruction. For real-time shape measurement, there are basically two approaches. The first approach is to use a single pattern, typically a color pattern. The use of this approach employs a color-encoded Moire technique for high-speed 3D surface contour retrieval. Other techniques use a rainbow 3D camera for high-speed 3D vision. Still others use a color structured light technique for high-speed scans of moving objects. Because these methods use color to code the patterns, the shape measurement result is affected to varying degrees by the variations of the object surface color. In general, better accuracy is obtained by using more patterns.

Another structured light approach for real-time shape measurement is the use of multiple coded patterns with rapid switching between them so that they could be captured in a short period of time. This approach has been used and develops a real-time 3D model measurement system that uses four patterns coded with stripe boundary codes. Some embodiments may provide an acquisition speed of about 15 fps, which is sufficient for scanning slowly moving objects. However, like any other binary-coding method, the spatial resolution of these methods is relatively low because the stripe width must be larger than one pixel. Moreover, switching the patterns by repeatedly loading patterns to the projector may limit the switching speed of the patterns and therefore the speed of shape measurement.

Another example of an optical detector is found in U.S. Pat. Nos. 6,788,210 and 6,438,272 (incorporated by reference herein), which provide a vision system for real-time and high-speed 3D shape measurement, with full capability of providing fast updating of the 3D surface maps and maps of the curves indicating the treatment areas and positioning markings such as tick marks of the said curves. In this manner, the sensor may serve to close the present automated debridement system control loop and as the means to provide for safe operation of the system, by for example, shutting the treatment laser beam off when the error between the actual position and desired position of the treatment laser beam is more than a selected (programmed) threshold. This method is based on a rapid phase-shilling technique. This technique uses three phase-shifted, sinusoidal grayscale fringe patterns to provide pixel-level resolution. The patterns are projected to the object with a switching speed of 240 fps. This system takes full advantage of the single-chip DLP technology for rapid switching of three coded fringe patterns. A color fringe pattern with its red, green, and blue channels coded with three different patterns is created by a PC. When this pattern is sent to a single-chip DLP projector, the projector projects the three-color channels in sequence repeatedly and rapidly. To eliminate the effect of color, color filters on the color wheel of the projector are removed. As a result, the projected fringe patterns are all in grayscale. A properly synchronized high-speed B/W CCD camera is used to capture the images of each color channel from which 3D information of the object surface is retrieved. A color CCD camera, which is synchronized with the projector and aligned with the B/W camera, is also used to take 2D color pictures of the object at a frame rate of 26.7 fps for texture mapping. Together with the fast 3D reconstruction algorithm and parallel processing software, high-resolution, real-time 3D shape measurement is realized at a frame rate of up to 40 fps and a resolution of 532×500 points per frame. Other systems for 3D shape measurement known in the art can also lie used in the system and methods of the present invention, such as those commercially available from Blue Hill Optical Technologies, located in Norwood, Mass. or Nutfield Technology, Windham, N. H.

For the projection of the computer-generated patterns, a single-chip DLP projector is used, which produces images based on a digital light switching technique. With this system, a complex facial surface has been mapped at 40 fps (the accuracy of the system being 0.1×0.1×0.1 mm), providing an excellent speed and resolution for the present automated laser debridement and treatment systems and the like.

The color image is produced by projecting the red, green, and blue channels sequentially and repeatedly at a high speed. The three color channels are then integrated into a full color image. To take advantage of this projection mechanism of a single-chip DLP projector, a color pattern which is a combination of three patterns in the red, green, and blue channels is created. The projector has no color filters for a monochrome mode of operation. As a result, when the color pattern is sent to the projector, it is projected as three grayscale patterns, switching rapidly from channel to channel at 240 fps. A high-speed B/W camera, which is synchronized with the projector, is used to capture the three patterns rapidly for real-time 3D shape measurement. An additional color camera is used to capture images for texture mapping. To obtain 3D maps and color information simultaneously, multi-threading programming is used to guarantee that two cameras work independently and that the timing of image grabbing is only determined by the external trigger signal.

For more realistic rendering of the object surface, a color texture mapping method may be used that is basal on a sinusoidal phase-shifting method. In this method, the three fringe patterns have a phase shift of $2\pi/3$ between neighboring patterns. Since averaging the three fringe patterns washes out the fringes, a color image can be obtained without fringes by setting the exposure time of the color camera to one projection cycle or 12.5 ms.

These systems provide the capability of rapidly projecting and capturing three coded patterns rapidly. The employed fast three-step phase-shifting method provides a real-time 3D reconstruction speed and high measurement accuracy of the order of 0.1×0.1×0.1 mm. The sinusoidal phase-shifting method that has been used extensively in optical metrology to measure 3D shapes of objects at various scales. In this method, a series of phase-shifted sinusoidal fringe patterns are recorded, from which the phase information at every pixel is obtained. This phase information helps determine the correspondence between the image field and the projection field. Once this correspondence is determined, the 3D coordinate information of the object can be retrieved based on triangulation. A number of different sinusoidal phase-shifting algorithms are available. A three-step phase-shifting algorithm similar to the traditional three-step algorithm may be used, which requires three phase-shifted images.

In some embodiments, the optical detector and printer are both mounted on a portable X-Y-Z plotting system.

C. Cells and Tissues.

Any type of cell may be printed using the methods herein, including, but not limited to, mammalian cells (including mouse, rat, dog, cat, monkey and human cells), including somatic cells, stem cells, progenitor cells and differentiated cells, without limitation. Stem cells have the ability to replicate through numerous population doublings (e.g., at least 60-80), in some cases essentially indefinitely, and also have the ability to differentiate into multiple cell types (e.g., is pluripotent or multipotent). It is also possible for cells to be transfected with a compound of interest that results in the cells becoming immortalized (i.e., able to double more than 50 times). For example, it has been reported that mammalian cell transfection with telomerase reverse transcriptase (hTERT) can immortalize neural progenitor cells (See U.S. Pat. No. 7,150,989 to Goldman et al.).

"Embryonic stem cell" as used herein refers to a cell that is derived from the inner cell mass of a blastocyst and that is pluripotent.

"Amniotic fluid stem cell" as used herein refers to a cell, or progeny of a cell, that (a) is found in, or is collected from, mammalian amniotic fluid, mammalian chorionic villus, and/or mammalian placental tissue, or any other suitable tissue or fluid from a mammalian donor, (b) is pluripotent; (c) has substantial proliferative potential, (d) optionally, but preferably, does not require feeder cell layers to grow in vitro, and/or (e) optionally, but preferably, specifically binds c-kit antibodies (particularly at the time of collection, as the ability of the cells to bind c-kit antibodies may be lost over time as the cells are grown in vitro).

"Pluripotent" as used herein refers to a cell that has complete differentiation versatility, e.g., the capacity to grow into any of the animal's cell types. A pluripotent cell can be self-renewing, and can remain dormant or quiescent with a tissue. Unlike a totipotent cell (e.g., a fertilized, diploid egg cell) a pluripotent cell cannot usually form a new blastocyst.

"Multipotent" as used herein refers to a cell that has the capacity to grow into any of a subset of the corresponding animal cell types. Unlike a pluripotent cell, a multipotent cell does not have the capacity to form all of the cell types of the corresponding animal.

Cells may be autologous (i.e., from the very subject to which they will be applied) syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogenic (i.e., from the subject to be treated) and isogeneic (i.e., a genetically identical but different subject, e.g., from an identical twin). Cells may be obtained from, e.g., a donor (either living or cadaveric) or derived from an established cell strain or cell line. For example, cells may be harvested from a donor using standard biopsy techniques known in the art.

According to some embodiments, at least a portion of the cells are viable after they are printed. "Viable cells" includes cells that adhere to a culture dish or other substrate and/or are capable of survival (e.g., proliferation). In some embodiments, at least 30, 40 or 50% of the total cells loaded are viable, and in further embodiments at least 60, 70, 80, or 90% or more of the total cells loaded are viable after printing. Cell viability may be measured by any conventional means, e.g., the MTS assay, and at a reasonable time after printing, e.g., 1 day after printing completion. Viability is measured upon incubation under conditions known in the art to be optimal for survival of the certain cells types present. For example, many eukaryotic cell types are typically incubated in a suitable medium at 5% carbon dioxide (95% atmospheric air) and 37 degrees Celsius.

Various mechanisms may be employed to facilitate the survival of the cells during and/or after printing. Specifically, compounds may be utilized that support the printed cells by providing hydration, nutrients, and/or structural support. These compounds may be applied to the substrate using conventional techniques, such as manually, in a wash or bath, through vapor deposition (e.g., physical or chemical vapor deposition), etc. These compounds may also be combined with the cells and/or compositions before and/or during printing, or may be printed or otherwise applied to the substrate (e.g., coated) as a separate layer beneath, above, and/or between cell layers. For example, one such support compound is a gel having a viscosity that is low enough under the printing conditions to pass through the nozzle of the print head, and that can gel to a stable shape during and/or after printing. Such viscosities are typically within the range of from about 0.5 to about 50 centipoise, in some embodiments from about 1 to about 20 centipoise, and in some embodiments, from about 1 to about 10 centipoise. Some examples of suitable gels that may be used in the present invention include, but are not limited to, agars, collagen, hydrogels, etc.

Another polymer used for hydrogels is alginate, a natural polysaccharide extracted from seaweed. One feature of alginate solutions is their gelling properties in the presence of divalent cations (e.g., Mg++, Ca++, Sr++, Ba++).

Besides gels, other support compounds may also be utilized in the present invention. Extracellular matrix analogs, for example, may be combined with support gels to optimize or functionalize the gel. In some embodiments, one or more growth factors may also be introduced in the printed arrays. For example, slow release microspheres that contain one or more growth factors in various concentrations and sequences may be combined with the cells and/or composition. Other suitable support compounds might include those that aid in avoiding apoptosis and necrosis of the developing structures. For example, survival factors (e.g., basic fibroblast growth factor) may be added. In addition, transient genetic modifications of cells having antiapoptotic (e.g., bcl-2 and telomerase) and/or blocking pathways may be included in compositions printed. Adhesives may also be utilized to assist in the survival of the cells after printing. For instance, soft tissue adhesives, such a cyanoacrylate esters, fibrin sealant, and/or gelatin-resorcinol-formaldehyde glues, may be utilized to inhibit nascent constructs from being washed off or moved following the printing of a layer. In addition, adhesives, such as arginine-glycine-aspartic acid (ROD) ligands, may enhance the adhesion of cells to a gelling polymer or other support compound. Extracellular proteins, extracellular protein analogs, etc., may also be utilized.

"Growth factor" may be any naturally occurring or synthetic growth factor, including combinations thereof, suitable for the particular tissue or array being printed. Numerous growth factors are known. Examples include, but are not limited to, insulin-like growth factor (e.g., IGF-1), transforming growth factor-beta (TGF-beta), bone-morphogenetic protein, fibroblast growth factor, platelet derived growth factor (PDGF), vascular endothelial growth factor (VEGF), connective tissue growth factor (CTGF), basic fibroblast growth factor (bFGF), epidermal growth factor, fibroblast growth factor (FGF) (numbers 1, 2 and 3), osteopontin, bone morphogenetic protein-2, growth hormones such as somatotropin, cellular attractants and attachment agents, etc., and mixtures thereof. See, e.g., U.S. Pat. Nos. 7,019,192; 6,995,013; and 6,923,833. For example, growth factor proteins may be provided in the printed composition and/or encoded by plasmids transfected into printed cells.

In some embodiments, cells, compositions, support compounds, and/or growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degradable support material), and some of the ingredients may be printed in the form of a second pattern (e.g., cells in a pattern different from the support, or two different cell types in a different pattern). The particular combination and manner of printing will depend upon the particular tissue being printed.

In some embodiments, cells/compositions are printed onto a substrate, e.g., a biocompatible scaffold, which may be subsequently implanted into or grafted onto a subject in need thereof. In other embodiments, cells/compositions of interest are directly printed in situ onto living tissues in the body, with or without prior substrate application (e.g., a layer of fibrin) in which the cells may attach.

In some embodiments, cells may be isolated from tissues of interest and cultured with techniques known in the art. "Isolated" as used herein signifies that the cells are placed into conditions other than their natural environment. Tissue or cells are "harvested" when initially isolated from a subject, e.g., a primary explant.

The "primary culture" is the first culture to become established alter seeding disaggregated cells or primary explants into a culture vessel. "Expanding" or "expansion" as used herein refers to an increase in number of viable cells. Expanding may be accomplished by, e.g., "growing" the cells through one or more cell cycles, wherein at least a portion of the cells divide to produce additional cells. "Growing" as used herein includes the culture of cells such that the cells remain viable, and may or may not include expansion and/or differentiation of the cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics (e.g., the ability to express a certain protein or marker).

"Express" or "expression" of a protein or other biological marker means that a gene encoding the same of a precursor thereof is transcribed, and preferably, translated. Typically, according to the present invention, expression of a coding region of a gene will result in production of the encoded polypeptide, such that the cell is "positive" for that protein or other downstream biological marker.

"Skin cells" include those cells normally found in skin, and include epidermal cells (e.g., keratinocytes, melanocytes, Merkel cells, Langerhan cells, etc., and any combination thereof) and dermal cells (e.g., fibroblasts, adipocytes, mast cells, macrophages, and any combination thereof). Skin tissue may be formed to mimic natural skin by the inclusion of melanocytes and dermal papilla cells. Skin tissue produced by the process of the present invention is useful for implantation into or on a subject to, for example, treat burns, and other wounds such as incisions, lacerations, and crush injuries (e.g., postsurgical wounds, and posttraumatic wounds, venous leg ulcers, diabetic foot ulcers, etc.)

"Muscle cells" include those cells normally found in muscle tissue, including smooth muscle cells, cardiac muscle cells, skeletal muscle cells (e.g., muscle fibers or myocytes, myoblasts, myotubes, etc.), and any combination thereof. Muscle cells/tissues produced by the processes described herein are useful for, among other things, the treatment of injuries or defects affecting muscle tissue, and/or promote muscle healing.

"Cartilage cells" include those cells normally found in cartilage, which cells include chondrocytes. "Chondrocytes" produce and maintain the extracellular matrix of cartilage, by, e.g., producing collagen and proteoglycans. Cartilage is a highly specialized connective tissue found throughout the body, and its primary function is to provide structural support for surrounding tissues (e.g., in the car and nose) or to cushion (e.g., in the trachea and articular joints). Types of cartilage include hyaline cartilage (articular joints, nose, trachea, intervertebral disks (NP), vertebral end plates), clastic cartilage (tendon insertion site, ligament insertion site, meniscus, intervertebral disks (AP)), costochondral cartilage (rib, growth plate), and fibrocartilage (ear). The loss of cartilage in a subject can be problematic, as it has a very limited repair capacity. "Mesenchymal stem cells" or "MSCs" are progenitors of chondrocytes. MSCs can also differentiate into osteoblasts. Cartilage cells/tissues produced by the processes described herein are useful for, among other things, implantation into a subject to treat cartilage injury or disease.

"Bone cells" include those cells normally found in bone, and include osteoblasts, osteoclasts, ostcocytes, and any combination thereof. Bone cells/tissues produced by the processes described herein are useful for, among other things, implantation into a subject to treat bone fractures or defects, and/or promote bone healing.

"Nervous system cells" or "nerve cells" include those cells normally found in the peripheral nervous system, including neuronal and glial cells.

"Vascular cells" include those cells normally found in the mammalian vasculature, including blood vessels, and include endothelial cells, smooth muscle cells and fibroblasts.

In some embodiments, stem cells are printed onto substrates by inkjet printing. Stem cells may be printed alone (typically in combination with a support compound or compounds) or in combination with one or more additional cells (e.g., in a combination selected to produce a tissue as described above). In some embodiments, stem cells are differentiated into cells of interest.

"Differentiation" and "differentiating" as used herein include (a) treatment of the cells to induce differentiation and completion of differentiation of the cells in response to such treatment, both prior to printing on a substrate, (b) treatment of the cells to induce differentiation, then printing of the cells on a substrate, and then differentiation of the cells in response to such treatment after they have been printed, (c) printing of the cells, simultaneously or sequentially, with a differentiation factors) that induces differentiation after the cells have been printed, (d) contacting the cells after printing to differentiation factors or media, etc., and combinations of all of the foregoing. In some embodiments, differentiation may be modulated or delayed by contacting an appropriate factor or factors to the cell in like manner as described above. In some embodiments appropriate differentiation factors are one or more of the growth factors described above. Differentiation and modulation of differentiation can be carried out in accordance with known techniques, e.g., as described in U.S. Pat. No. 6,589,728, or U.S. Patent Application Publication Nos.: 2006006018 (endogenous repair factor production promoters); 20060013804 (modulation of stem cell differentiation by modulation of caspase-3 activity); 20050266553 (methods of regulating differentiation in stem cells); 20050227353 (methods of inducing differentiation of stem cells); 20050202428 (pluripotent stem cells); 20050153941 (cell differentiation inhibiting agent, cell culture method using the same, culture medium, and cultured cell line); 20050131212 (neural regeneration peptides and methods for their use in treatment of brain damage); 20040241856 (methods and compositions for modulating stem cells); 20040214319 (methods of regulating differentiation in stem cells); 20040161412 (cell-based VEGF delivery); 20040115810 (stem cell differentiation-inducing promoter); 20040053869 (stem cell differentiation); or variations of the above or below that will be apparent to those skilled in the art.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

"Treat" refers to any type of treatment that imparts a benefit to a subject, e.g., a patient afflicted with a trauma or disease. Treating includes actions taken and actions refrained from being taken for live purpose of improving the condition of the patient (e.g., the promotion of healing and/or formation of tissues on a patient in need thereof, the relief of one or more symptoms, etc.). In some embodiments, treating includes reconstructing skin tissue (e.g., where such tissue has been damaged or lost by injury or disease) by directly printing cells and/or tissues onto a subject in need thereof.

The present invention provides for the printing of tissues by the appropriate combination of cell and support material, or two or three or more different cell types typically found in a common tissue (e.g., skin tissue). Cells, support compounds, and growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degradable support material), and some of the ingredients may be printed in the form of a second pattern (e.g., cells in a pattern different from the support, or two different cell types in a different pattern). Again, the particular combination and manner of printing will depend upon the particular tissue. Materials to be printed for specific tissues or tissue substitutes are described further below.

Skin. In representative embodiments, to produce epidermal-like skin tissue, the following are printed:
- (a) at least one cell type, and preferably at least two or in some embodiments three or four different epidermal cell types (e.g., keratinocytes, melanocytes, Merkel cells, Langerhan cells, etc., and any combination thereof); and/or
- (b) at least one support compound such as described above (e.g., collagen, elastin, keratin, etc., and any combination thereof); and/or
- (c) at least one growth factor as described above (e.g., basic fibroblast growth factor (bFGF), Insulin-Like Growth Factor 1, epidermal growth factor (EGF), etc., and any combination thereof);

In some embodiments the epidermal cells, support compound and/or growth factors printed as described above (which form an "epidermal" type layer) are printed on, or on top of, a previously formed (e.g., printed or ink-jet printed) "dermal" type layer, the previously printed dermal layer layers comprising: (a) one, two, three or four different dermal cells (fibroblasts, adipocytes, mast cells, and/or macrophages), (b) at least one support compound as described above; and/or (c) at least one growth factor as described above.

Skin tissue produced by the process of the present invention is useful for treatment of, for example, burns, and other wounds such as incisions, lacerations, and crush injuries (e.g., postsurgical wounds, and posttraumatic wounds, venous leg ulcers, diabetic foot ulcers, etc.).

Bone. In particular embodiments, to produce bone tissues, the following are printed:
- (a) at least one bone cell type, and preferably at least two or three different bone cell types (e.g., osteoblasts, osteoclasts, osteocytes, and any combination thereof, but in some embodiments at least osteoblasts and osteoclasts, and in some embodiments all three); and/or
- (b) at least one support compound such as described above (e.g., collagen, hydroxyapatites, calicite, silica, ceramic, proteoglycans, glycoproteins, etc., and any combination thereof); and/or
- (c) at least one growth factor (e.g., bone morphogenetic protein, transforming growth factor, fibroblast growth factors, platelet-derived growth factors, insulin-like growth factors, etc., and any combination thereof).

Bone tissues produced by the processes described herein are useful for, among other things, implantation into a subject to treat bone fractures or defects, and/or promote bone healing.

Nerve. In representative embodiments, to produce nerve tissue, the following are printed:
- (a) at least one, two or three cells types, and preferably (i) peripheral nerve cells and/or (ii) at least one glial cell type and (iii) any combination thereof (e.g., a combination of at least one nerve cell and at least one glial cell); and/or
- (b) at least one support compound such as described above; (e.g., laminin, collagen type IV, fibronectin, etc., and any combination thereof); and/or
- (c) at least one growth factor (e.g., NGF, brain-derived neurotrophic factor, insulin-like growth factor-1, fibroblast growth factor, etc., or any combination thereof); and any combination of the foregoing.

Nerve tissue produced by the processes described herein is useful, among other things, to treat nerve injury or degenerative diseases affecting the peripheral nervous system.

Muscle. In representative embodiments, to produce muscle tissue, the following are printed:
- (a) at least one muscle cell type; and/or
- (b) at least one support compound such as described above; (e.g., laminin, collagen type IV, fibronectin, etc., and any combination thereof); and/or
- (c) at least one growth factor (e.g., vascular endothelial growth factor, insulin-like growth factors (IGFs), etc., or any combination thereof); and any combination of the foregoing.

Muscle tissue produced by the processes described herein is useful, among other things, to treat smooth muscle, skeletal muscle or cardiac muscle injury or diseases affecting these tissues.

Vascular tissue. In representative embodiments, to produce vascular tissue, the following are printed:
- (a) at least one vascular cell type, and preferably at least two or three different vascular cell types (e.g., endothelial cells, smooth muscle cells, fibroblasts, and any combination thereof, but in some embodiments at least endothelial cells, smooth muscle cells, and in some embodiments all three); and/or
- (b) at least one support compound such as described above; (e.g., laminin, collagen type IV, fibronectin, etc., and any combination thereof); and/or
- (c) at least one growth factor (e.g., vascular endothelial growth factor, insulin-like growth factors (IGFs), etc., or any combination thereof); and any combination of the foregoing.

Vascular tissue produced by the processes described herein is useful, among other things, to form vascular networks and/or treat injury or diseases affecting these tissues.

In some embodiments, the tissue is created "in sequence" layer-by-layer, with a printed layer (A), then a printed layer (B), and so on as needed in series, such as layers:

ABCD . . .

Each layer may comprise cells, support compounds, growth factors, combinations thereof, etc., as desired to construct the tissue as needed or desired.

In some embodiments, cells may be printed in a first layer, followed by a second layer of support materials such as a gel, optionally followed by a third layer of cells. For example, a multiple layered skin tissue may be printed as a layer comprising fibroblasts, followed by a layer comprising a gel (e.g., comprising fibrin, fibrinogen, collagen, etc.), followed by a layer comprising keratinocytes. Additional layers may also be provided as desired. Thrombin may also be printed with or onto one or more layers, if desired.

In some embodiments, skin cells and/or layers thereof can be printed (e.g., fibroblasts, keratinocytes, melanocytes, etc.), and additional skin cells printed thereon or therewith in discrete units and/or patterns. For example, papilla cells, which form hair follicles, in some embodiments may be printed at specific locations and/or densities (hair shaft thickness and length being at least in part determined by dermal papilla cell number and volume, with hairs becoming longer with increasing cell number), which can generate hair more closely approximating that from the native skin tissue for different body locations, age groups, genders, etc. Outer root cells may also be printed with the dermal papilla cells, if desired. Melanocytes may also be printed at specific locations and/or densities as desired, for example, to better match adjoining skin (e.g., with freckles).

In some embodiments, use of these cell printing patterns may also aid in regeneration of old wounds that already have scars, replacing the scars with more natural-looking skin.

D. Methods of Data Processing, Computer Programs and Systems.

In some embodiments, data obtained from the optical detector is pieced together to form a model of the bodily surface of interest (e.g., a wound surface). The bodily surface may be of any body portion, including a hand, foot, arm, leg, torso, chest, abdomen, back, head, face, portions thereof and/or combinations thereof, etc., including a wound area on the same.

In some embodiments, the surface is then transformed into a mold of the surface. A "mold" as used herein is a three-dimensional representation of the bodily surface of interest, which in some embodiments may be displayed visually, and which may also include, in addition to three-dimensional map coordinates, information such as color and/or infrared radiation intensity, among others. The mold according to some embodiments is interpreted into a "negative" mold, in which the layers are reversed, and may be further split into layers on the Z axis to determine which layers correspond to the natural tissue layers (e.g., dermis and epidermis layers of skin tissue), as necessary to guide the associated printer.

In some embodiments, each layer is overlaid with a series of lines (i.e., the lines are added to the layer representation or mold) that cover at least a portion of the area detected. These lines may then be used (e.g., by control software) to determine a path for the printer. The printer may print along the series of lines for each layer, thus forming a tissue in a layer-by-layer fashion.

In some embodiments, the user can define a series of bitmap images where each non-black pixel corresponds to a cell drop, and the color of the pixel corresponds to the cell type to print. This allows the user to create complex structures using various cell types and/or in various configurations.

System and/or component operation according to some embodiments may be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the desired operations.

These computer program instructions may also be stored in a computer-readable memory that can direct a computer or other programmable data processing apparatus to function in a particular manner, such that the instructions stored in the computer-readable memory produce an article of manufacture including instructions which implement the operations.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the operations.

Accordingly, the present invention may be embodied in hardware and/or in software (including firmware, resident software, micro-code, etc.). Furthermore, embodiments of the present invention may take the form of a computer program product on a computer-usable and/or computer-readable storage medium having computer-usable or computer-readable program code embodied in the medium for use by or in connection with an instruction execution system. As used herein, a computer-usable or computer-readable medium may be any medium that can contain or store the program for use by or in connection with the instruction execution system, apparatus, or device.

The computer-usable and/or computer-readable medium may be, for example but not limited to, an electronic, magnetic, optical, electromagnetic, infrared, or semiconductor system, apparatus or device. More specific examples (a non-exhaustive list) of the computer-readable medium would include the following: a portable computer diskette, a random access memory (RAM), a read-only memory (ROM), an erasable programmable read-only memory (EPROM or Flash memory), and a portable compact disc read-only memory (CD-ROM).

In some embodiments, software employs a three-tiered architecture design. The three-tiered architecture handles three areas of communication: between the user and the software; among the software components; and between the software and the file system. This design structure may allow individual components to be quickly and easily altered as necessary without affecting the other components.

In some embodiments, data gathered from the optical detector are represented as an object (e.g., a skin object). Each object may comprise one or more layers of the tissue, and each layer may be broken into a grid that encapsulates the individual lines from detector. This representation may significantly reduce the time necessary to deliver skin by allowing the delivery system to prim points from one piece of the grid while the computer analyzes the next piece. In some embodiments, points from the object are passed in a generic format to the delivery system where they are parsed for printing in a manner that incorporates the locations of the different cell types in the printhead. This implementation may allow the user to quickly define enhancements to the scanned data and include other components of the tissue (e.g., skin components such as melanocytes and hair follicles for skin tissue).

The skin delivery system may be controlled by software employing a three-tiered architecture design. In some embodiments, the architecture may be based on the Microsoft .NET Framework 2.0 (Microsoft Corp., Redmond, WA). Some embodiments provide that the software may be written in any one or combination of programming languages, including object-oriented programming languages such as, for example, C++, among others. The three-tiered architecture may be configured to handle three areas of communications: between the user and the software; among the software components; and between the software and the file system. This design structure may allow every component to be quickly and easily altered as necessary without affecting the other components. Furthermore, because the software is not based on a proprietary system such as, for example, MATLAB®, it can be deployed to any computer capable of running the .NET Framework 2.0.

The present invention is explained in greater detail in the following non-limiting examples.

Example 1

This example describes the design and use of a novel delivery system for in situ bioprinting of the skin. The cartridge based system presented here can be easily transported from patient to patient and can rapidly print skin constructs that mimic normal skin. The device allows for rapid on-site management of burn wounds, integrating a method to determine the size, shape, and depth of a wound with controlled delivery of skin cells to the target wound site in situ. This integration allows the system to effectively manage the treatment of large injuries while reconstructing the normal skin structure. A proof-of-concept experiment using in situ delivery of fibroblasts and keratinocytes to a mouse model of large skin wounds described below demonstrates its efficacy.

Materials and Methods

The following criteria were established to guide the hardware design for this exemplary system:
1. The system should be portable and capable of being quickly transported to the wounded personnel and it should be easily converted for use in different patients with different needs. For example, the system should be capable of fitting through hospital doors and hallways, and it should be constructed from lightweight materials for easy transport.
2. The system should be capable of easy sterilization.
3. The system should be capable of tailoring cell therapy to a patient's specific needs.
4. The system should allow for a wide range of body types.
5. The system should be capable of repeated use.
6. Maintenance of the system should be relatively easy and inexpensive.

We have accomplished these goals by using a cartridge based delivery system with a laser scanning system, both mounted on a portable XYZ plotting system (FIG. 1). The cartridge system is similar to that used in traditional inkjet printing such that each cell type is loaded into an individual cartridge in the same way different color inks would be contained in different cartridges. However, standard inkjet printing connects one printhead to one cartridge, while the skin delivery system allows each cartridge to connect to multiple printheads. This type of configuration allows arbitrary printhead configurations that can conform to each patient's specific needs. It also increases the throughput of the system and provides a rapid method of sterilization by attaching a cartridge of cleaning fluid to the printheads.

The printheads in the novel device use pressure-based nozzles instead of the thermal or piezoelectric microfluidic delivery devices used in traditional inkjet printers. A pressure-based delivery system allows the printer to remain a safe distance above the patient to accommodate a variety of body types.

Tailoring cell therapy to individual patients requires length, width, and depth information about the wound. This system incorporates a three-dimensional laser scanner (NexEngine Inc., Santa Monica, CA) mounted above the patient. This scanner can be moved to various locations on the body, and information about the wound is gathered with an accuracy of approximately 127 μm.

The cartridges, printheads, and scanner are mounted on the Z axis of a belt-driven plotting system (FIG. 1) capable of 100 μm movements. The Y axis moves the X axis which in turn moves the Z axis. Since the X and Y axes comprise the majority of the system's weight this configuration allows those axes to remain stationary while permitting the system to accommodate a wide range of body types.

The plotting system is mounted on a mobile frame. Patients with massive burn injuries are difficult to transport and some current treatments, including INTEGRA® and autologous keratinocyte culture, require multiple procedures. Multiple procedures require the fragile patient to be moved between the bed and the operating room for a number of times. This frame is designed to alleviate transport concerns by allowing the system to quickly move to patient beds and operating rooms.

Software

The skin delivery system is controlled by software employing a three-tiered architecture design based on the Microsoft .NET Framework 2.0 (Microsoft Corp., Redmond, WA) and was written in C++. The three-tiered architecture handles three areas of communication: between the user and the software, among the software components, and between the software and the file system. This design structure allows every component to be quickly and easily altered as necessary without affecting the other components. Furthermore, because the software is not based on a proprietary system such as MATLAB®, it can be deployed to any computer capable of running the .NET Framework 2.0.

The data obtained from the laser scanner is pieced together to form a model of the wound surface. This surface is transformed into a negative mold of the wound which is split into layers on the Z axis to determine which layers correspond to the dermis and epidermis. Each layer is overlaid with a series of lines that cover the entire wound area. These lines are used by the control software to determine a path for the printer.

Each of the smaller components of the software follows a design pattern similar to the overall architecture. Data gathered from the laser scanner are represented as a skin object. Each skin object consists of skin layers, and each layer is broken into a grid that encapsulates the individual lines from the scanner. This representation significantly reduces the time necessary to delivery skin by allowing the delivery system to print points from one piece of the grid while the computer analyzes the next piece. Points from the skin object are passed in a generic format to the delivery system where they are parsed for printing in a manner that incorporates the locations of the different cell types in the printhead. This implementation allows the user to quickly define enhancements to the scanned data and include other important skin components such as melanocytes and hair follicles.

Animal Model and Testing

All animal procedures were performed according to the protocols approved by the Wake Forest University Health Sciences Animal Care and Use Committee. The skin delivery system prototype was evaluated by creating a 3×2.5 cm (L×W) full-thickness skin defect on the dorsa of six female outbred athymic nude (Nu/nu) mice (Charles River Laboratories, Raleigh, NC). This defect represents approximately a 50% TBSA wound. Three mice were untreated and the others were treated by cell printing. Human fibroblasts were obtained from human foreskin and cultured in high glucose Dulbecco's modified Eagle's medium (Gibco-BRL Grand Island, NY) with 5% fetal bovine serum and 1% antibiotics. Human keratinocytes were obtained from ScienCell (Carlsbad, CA) and cultured in keratinocyte serum-free media (Gibco-BRL) with 1% antibiotics. When sufficient cell numbers were reached, cells were trypsinized for 5 min and suspended in a mixture of 25 mg/mL fibrinogen and 1.1 mg/mL type I collagen in phosphate-buffered saline. One layer of fibroblasts (passage 6) was printed at 250,000 cells cm$^{-2}$ followed by an equal amount of 20 IU/mL thrombin. The thrombin was allowed to react for 15 minutes before a layer of keratinocytes (passage 5) was printed at 500,000 cells cm$^{-2}$, again followed by thrombin. Each wound received antibiotic cream and was covered with sterile cotton gauze wrapped in surgical tape to prevent removal by the mouse. Wound coverings were changed at 1 week and removed at 2 weeks post-surgery. Fibroblasts and keratinocytes given to one mouse were prelabeled with the fluorescent dyes PKH 26 (red) and PKH67 (green) (Sigma-Aldrich, St. Louis, CO), and this mouse along with one untreated mouse were sacrificed at 1 week for retrieval of the wound area to determine if the labeled cells were present in the construct. The wound size for the experiment with labeled cells was 1.5×2 cm (L×W) for proof of concept. For the other two mice, each 3×2.5 cm wound was evaluated every week for 3 weeks to determine the size of the wound and the extent of scarring. At 3 weeks the scar tissue was removed for histological evaluation.

Results

Figure 9:
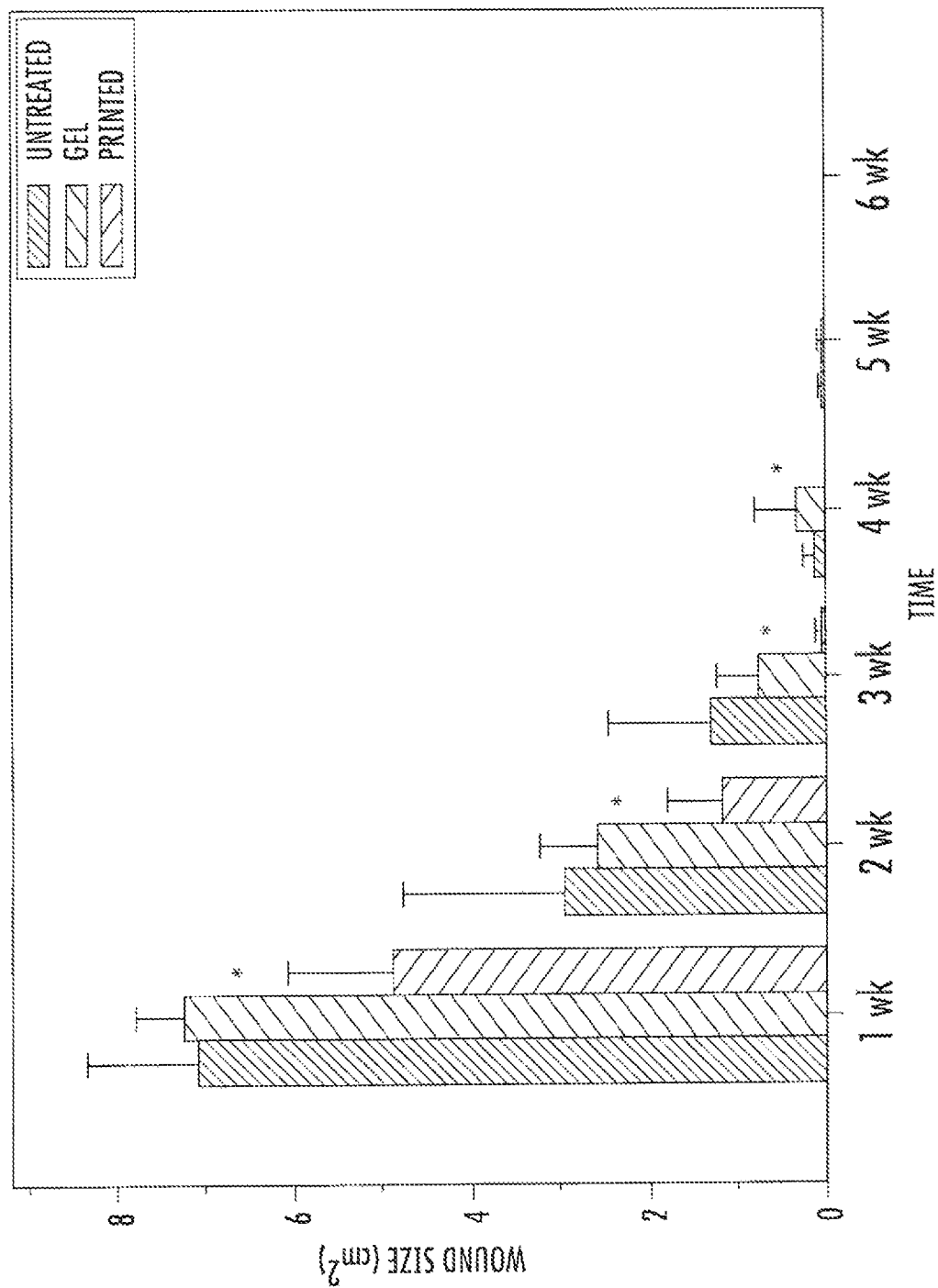
FIG. 9. Skin repair using bioprinting shows significant difference in wound size between 1 and 4 weeks after injury (p<0.05).

The skin delivery system is capable of printing skin cells directly onto a lull-thickness defect on nude mice. Skin constructs printed with fluorescent prelabeled cells and retrieved after 1 week showed the presence of labeled cells within the wound bed (data not shown). These cells appeared to participate in the healing process, as near-complete closure of the wound occurred at 2 weeks, and complete wound closure occurred at 3 weeks (data not shown). H&E staining of the skin constructs at 3 weeks demonstrated structural similarity to normal skin, with organization of the keratinocytes into epidermal strata and the fibroblasts into dermis (data not shown). The untreated mouse showed wound healing in the same timeframe but did not demonstrate complete wound closure as seen in the printed mice. In addition, the center of the untreated wound shows inflammation and scabbing at 3 weeks whereas the covered wound shows cellular integration into the surrounding skin. Results are shown in FIG. 9.

Discussion

Our skin delivery system allows rapid production of patient-specific wound coverage while simultaneously obviating the need for specialized manufacturing facilities and cell culture materials at burn care centers. Furthermore, the delivery system fulfills many of the criteria for an ideal skin substitute as demonstrated by previous uses of allogeneic skin cells for burn coverage. Cells printed using the delivery system adhere intimately to the wound bed, provide a non-antigenic microbial barrier, participate in normal host repair mechanisms, maintain elasticity and long-term durability, display long-term mechanical and cosmetic function comparable to split-thickness autografts, require a single operation, are inexpensive, and have minimal storage requirements. The only ideal skin substitute characteristic that is not fulfilled by this system is the requirement of indefinite storage, which is virtually impossible to achieve with any living skin substitute. However, the cartridge system allows packing and shipping of allogeneic cells to burn centers, which in turn allows treatment of the wound as soon as the patient is stable and the wound has undergone debridement. In contrast, a typical autologous grail requires 2-5 weeks to grow in culture.

We demonstrated proof-of-concept by printing a two-layer skin construct consisting of fibroblasts and keratinocytes directly into a full-thickness skin defect on a nude mouse. This printing was performed by delivering specific cells to specific target areas.

We embedded the cells in a matrix of fibrinogen and type I collagen for two reasons. First, the formation of fibrin from the reaction of fibrinogen and thrombin provides a strong gel that allows the cells to maintain their position on the mouse even if the mouse moves. Second, fibrin and type I collagen have already been used to create skin constructs. After printing, prelabeled fibroblasts and keratinocytes were visible in the construct 1 week post-printing, indicating that the cells remained in the wound area. Evaluation of the wound area over 3 weeks showed rapid closure of the wound in the treated mouse as compared to the untreated mouse. The remaining open wound in the printed group at 2 weeks post-surgery was open only at the center of the wound in the area of greatest body curvature. This could be due to the possibility that the printed cell droplets rolled off the curvature. One way to correct for this may be by replacing the thrombin delivery system with a nebulizer to rapidly create fibrin.

H&E staining of the printed constructs showed organization of the cells into a structure similar to normal skin. The epidermis was the same thickness in both the printed construct and normal tissue. There was a demarcation at the dermal-epidermal junction and the dermis in the printed construct appeared to be similar in composition to the normal tissue. This shows the ability of the skin delivery system to print tissue that mimics the normal skin structure.

While this study only examined the use of fibroblasts and keratinocytes in skin printing, the design of the system allows for precise delivery of additional cell types. These include, but are not limited to, follicular cells, melanocytes, and endothelial cells. Including these additional cell types could further mimic the normal skin structure and provide functional and cosmetic improvements over current treatment techniques, especially with regard to pigmentation and vascularization. The print cartridges can also be designed to include factors aimed at improving the function of the skin constructs. These include scarless healing reagents, growth factors, and protease inhibitors to maintain the longevity of other reagents. If a cell type or reagent can be packaged into a cartridge, our system can rapidly deliver that cell or reagent to a specific location on the patient. This properly makes our system superior to most current burn treatments because it eliminates the need for culturing cells and reagents in a graft construct prior to patient transplantation.

The foregoing is illustrative of the present invention, and is not to be construed as limiting thereof. The invention is defined by the following claims, with equivalents of the claims to be included therein.

That which is claimed is:

1. A delivery system configured to control a three-dimensional optical detector and a printer operatively coupled to the three-dimensional optical detector, the delivery system comprising:
   means for interpreting data from the optical detector to form a map of an area of interest of a patient;
   means for transforming the map into a negative mold of the area of interest, wherein the mold comprises a plurality of Z-axis layers; and
   means for overlaying each of the Z-axis layers of the negative mold with a series of lines, wherein the lines provide a path for control software to use to control the printer to deliver cells and/or compositions to the area of interest in situ based upon the map,
wherein the map is updated in real-time during delivery, by the printer, of the cells and/or compositions.

2. A delivery system comprising:
a three-dimensional optical detector;
a printer operatively coupled to the three-dimensional optical detector; and
a computing system comprising:
  a processor; and
  a memory coupled to the processor and comprising computer readable program code that when executed by the processor causes the processor to perform operations comprising:
interpreting data from the optical detector to form a map of an area of interest of a patient;
transforming the map into a negative mold of the area of interest, wherein the mold comprises a plurality of Z-axis layers; and
overlaying each of the Z-axis layers of the negative mold with a series of lines, wherein the lines provide a path for control software to use to control the printer to deliver cells and/or compositions to the area of interest in situ based upon the map,
wherein the map is updated in real-time during delivery, by the printer, of the cells and/or compositions.

3. The delivery system of claim 2, further comprising a surgical device that is configured to provide the optical detector and/or the printer with access to the area of interest of the patient.

4. The delivery system of claim 3, wherein the surgical device is an endoscopic device.

5. The delivery system of claim 2, wherein the area of interest comprises an injury or disease of the patient.

6. The delivery system of claim 2, wherein the data from the optical detector is represented as an object including the Z-axis layers, and
  wherein each of the Z-axis layers are represented by a grid that comprises the lines.

7. The delivery system of claim 6, wherein the operations further comprise directing the printer to deliver cells to a first location of the area of interest that is associated with a first piece of the grid representing the object while analyzing a second piece of the grid.

8. The delivery system of claim 6, wherein the operations further comprise parsing the object in a manner that incorporates locations of different cells and/or compositions to be printed by the printer.

9. The delivery system of claim 2, wherein the area of interest is a closed wound.

10. The delivery system of claim 2, wherein the cells are selected from the group consisting of cartilage cells, bone cells, muscle cells, vascular cells, skin cells, and combinations thereof.

11. The delivery system of claim 2, wherein the Z-axis layers correspond to one or more tissue layers.

12. A computer program product for processing data of an area of interest of a patient obtained from a three-dimensional optical detector to provide a path to a printer operatively coupled to the three-dimensional optical detector, the computer program product comprising a non-transitory computer readable medium having computer readable program code embodied therein, the computer readable program code comprising:
computer readable program code that interprets data from the optical detector to form a map of the area of interest of the patient;
computer readable program code that transforms the map into a negative mold of the area of interest, wherein the mold comprises a plurality of Z-axis layers; and
computer readable program code that overlays each of the Z-axis layers of the negative mold with a series of lines, wherein the lines provide a path for control software to use to control the printer to deliver cells and/or compositions to the area of interest in situ based upon the map,
wherein the map is updated in real-time during delivery, by the printer, of the cells and/or compositions.

13. The computer program product of claim 12, wherein the data from the optical detector is represented as an object including the Z-axis layers, and
  wherein each of the Z-axis layers are represented by a grid that comprises the lines.

14. The computer program product of claim 11, wherein the computer readable program code is further configured to direct the printer to deliver cells to a first location of the area of interest that is associated with a first piece of the grid representing the object while analyzing a second piece of the grid.

15. The computer program product of claim 13, further comprising computer readable program code that parses the object in a manner that incorporates locations of different cells and/or compositions to be printed by the printer.

16. The computer program product of claim 12, wherein the area of interest is a closed wound.

17. The computer program product of claim 12, wherein the computer readable program code is further configured to control a surgical device to provide the optical detector and/or the printer with access to the area of interest.

18. The computer program product of claim 17, wherein the surgical device is an endoscopic device.

19. The computer program product of claim 12, wherein the area of interest comprises an injury or disease of the patient.

20. The computer program product of claim 12, wherein the Z-axis layers correspond to one or more tissue layers.

* * * * *

UNITED STATES PATENT AND TRADEMARK OFFICE
CERTIFICATE OF CORRECTION

| | | |
|---|---|---|
| PATENT NO. | : 12,268,467 B2 | Page 1 of 1 |
| APPLICATION NO. | : 16/694017 | |
| DATED | : April 8, 2025 | |
| INVENTOR(S) | : Yoo et al. | |

It is certified that error appears in the above-identified patent and that said Letters Patent is hereby corrected as shown below:

On the Title Page

(56) References Cited, OTHER PUBLICATIONS, Page 2, Column 2, Binder KK cite, Line 70: Please correct "Binder KK" to read --Binder KW--

In the Specification

Column 1, Line 66: Please correct "(1))" to read --(b)--

Column 15, Line 67: Please correct "(ROD)" to read --(RGD)--

In the Claims

Column 28, Line 30, Claim 14: Please correct "claim 11" to read --claim 13--

Signed and Sealed this
Eleventh Day of November, 2025

John A. Squires
*Director of the United States Patent and Trademark Office*